US008361723B2

(12) United States Patent
Omary et al.

(10) Patent No.: US 8,361,723 B2
(45) Date of Patent: Jan. 29, 2013

(54) KERATIN 8 MUTATIONS ARE RISK FACTORS FOR DEVELOPING LIVER DISEASE OF MULTIPLE ETIOLOGIES

(75) Inventors: M. Bishr Omary, Ann Arbor, MI (US); Nam-On Ku, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/908,548

(22) Filed: Oct. 20, 2010

(65) Prior Publication Data

US 2011/0055937 A1 Mar. 3, 2011

Related U.S. Application Data

(62) Division of application No. 10/552,949, filed as application No. PCT/US2004/011533 on Apr. 14, 2004, now Pat. No. 7,838,217.

(60) Provisional application No. 60/462,989, filed on Apr. 14, 2003.

(51) Int. Cl.
*C12Q 1/68* (2006.01)
*C12P 19/34* (2006.01)
*C07H 21/02* (2006.01)
*C07H 21/04* (2006.01)
*C07K 14/435* (2006.01)

(52) U.S. Cl. ........... 435/6.11; 435/4; 435/6.1; 435/6.12; 435/6.17; 435/7.1; 536/23.5; 536/24.31; 536/24.33; 530/357

(58) Field of Classification Search .................. None
See application file for complete search history.

(56) References Cited

U.S. PATENT DOCUMENTS 7,838,217 B1 * 11/2010 Omary et al. ................ 435/6.16

OTHER PUBLICATIONS

Gene Card for Keratin 8 available via url: <genecards.org/cgi-bin/carddisp.pl?gene=krt8>, printed Sep. 26, 2011.*
Genbank Accession No. NM_002273, (Nov. 18, 2006).
Gene Card for keratin 8 available via url: <genecards.org/cgi-bin/carddisp.pl?gene=krt8>, (Sep. 26, 2011).
Halangk et al., "Keratin 8 Y54H and G62C mutations are not associated with liver disease", Journal of Medical Genetics, 41:e92 (2004).
Halushka et al., "Patterns of single-nucleotide polymorphisms in candidate genes for blood-pressure homeostasis", Nature Genetics, 22:239-247 (Jul. 1999).
Hesse et al., "A frequent keratin 8 p. L227L polymorphism, but no point mutations in keratin 8 and 18 genes, in patients with various liver disorders", Journal of Medical Genetics, 41:e42 (2004).
Hirschhorn et al., "A comprehensive review of genetic association studies", Genetics in Medicine, 4(2):45-61 (Mar. 2002).
Hunkapillar et al., "Large-scale and automated DNA sequence determination", Science, 254:59-74 (1991).
Irvine et al., "Human keratin diseases: the increasing spectrum of disease and subtlety of the phenotype-genotype correlation", British Journal of Dermatology, 140:815-828 (1999).
Ku et al., "Mutation of human keratin 18 in association with crytogenic cirrhosis", The Journal of Clinical Investigation, 99(1):19-23 (1997).
Ku et al., "Keratin mutations predispose to cryptogenic and noncryptogenic liver disease", Gastroenterology, 122(4): Suppl. 1, p. 80 (2002).
Ku et al., "Keratin 8 and 18 mutations associate with a broad range of human liver diseases", Molecular Biology of the Cell, 12:Supplennent, p. 56A (2001).
Ku et al., "Keratin 8 mutations in patients with cryptogenic liver disease", The New England J. of Med., 344(21):1580-1587 (2001).
Ku et al., "Keratin 8 and 18 mutations are risk factors for developing liver disease of multiple etiologies", PNAS, 100(10):6063-6068 (2003).
Strnad et al., "Keratin variants associate with progression of fibrosis during chronic Hepatitis C Infection," The American Association for the Study of Liver Disease, published online in Wiley InterScience (www.interscience.wiley.com); Hepatology 43(6): 1354-1363 (2006).
International Preliminary Report on Patentability dated Mar. 7, 2006 in International Patent Application No. PCT/US04/11533.
Written Opinion dated Sep. 6, 2005 in International Patent Application No. PCT/US04/11533.

* cited by examiner

Primary Examiner — Carla Myers
(74) Attorney, Agent, or Firm — Marshall, Gerstein & Borun LLP

(57) ABSTRACT

Keratin 8 and 18 (K8/K18) mutations are shown to be associated with a predisposition to liver or biliary tract disease, particularly noncryptogenic hepatobiliary disease. Unique K8/K18 mutations are shown in patients with diseases including but without limitation to viral hepatitis, biliary atresia, alcoholic cirrhosis and other acute or chronic toxic liver injury, cryptogenic cirrhosis, acute fulminant hepatitis, autoimmune liver disease, cystic fibrosis, primary biliary cirrhosis, primary sclerosing cholangitis, diseases that are linked with cryptogenic cirrhosis, such as nonalcoholic steatohepatitis, and the like. Livers with keratin mutations had increased incidence of cytoplasmic filamentous deposits. Therefore, K8/K18 are susceptibility genes for developing cryptogenic and noncryptogenic forms of liver disease. Mutant alleles are associated with disease susceptibility, and their detection is used in the diagnosis of a predisposition to these conditions.

5 Claims, 6 Drawing Sheets

A.

B.

KERATIN 8 MUTATIONS ARE RISK FACTORS FOR DEVELOPING LIVER DISEASE OF MULTIPLE ETIOLOGIES

FEDERALLY-SPONSORED RESEARCH OR DEVELOPMENT

This invention was made with Government support under contracts DK047918 and DK007056 awarded by the National Institutes of Health and with support from the Department of Veteran's Affairs. The Government has certain rights in this invention.

INTRODUCTION

Keratin mutations are associated with several skin, oral, esophageal, ocular and cryptogenic liver diseases that reflect tissue-specific expression of the particular keratin involved. The resulting cellular and tissue defects are manifestations of the clearly defined function of keratins that provides cells with the ability to cope with mechanical stresses. This keratin cytoprotective effect is evident in the blistering phenotype of several human keratin skin diseases such as epidermolysis bullosa simplex, and the phenotypes of animal models that lack or express a mutant keratin. Also, emerging evidence suggests that keratins protect cells from nonmechanical forms of injury via several mechanisms that may include: keratin regulation of cell signaling cascades, regulation of apoptosis, regulation of the availability of other cellular proteins, and protein targeting to subcellular compartments.

The function of keratins in protecting cells from mechanical stress is related to their unique properties and abundance as one of three major cytoskeletal protein families, which include intermediate filaments (IF), microfilaments and microtubules. Keratins (K) are members of the IF protein family, and are specifically expressed in epithelial cells and their appendages. They consist of >20 members (K1-K20), and are further classified into type I (K9-K20) and type II (K1-K8) keratins which form obligate, noncovalent heteropolymers. Keratins serve as important cell-type-specific markers. For example, unique keratin complements distinguish different epithelial cell types and thereby reflect epithelial subtype-specific diseases that result from keratin-specific mutations. As such, keratinocytes express K5/K14 basally and K1/K10 suprabasally, and hepatocytes express K8/K18. K8/K18 are also found in other glandular cells including enterocytes, with variable complements of K19/K20/K7 depending on the cell type.

Most keratin diseases are autosomal-dominant with near complete penetrance. Exceptions appear to be K18 and K8 mutations in patients with cryptogenic cirrhosis. To date, 6 patients have been described with K8 (5 patients) or K18 (1 patient) mutations, from a group of 55 patients with cryptogenic cirrhosis. Most patients with cryptogenic cirrhosis, including those with K8/K18 mutations, do not have a well-defined liver disease family history. Absence of a clear family history suggests that K8/K18 mutations predispose to, rather than cause, liver disease. The presence and frequency of keratin mutations in noncryptogenic liver disease is heretofore unknown.

SUMMARY OF THE INVENTION

Keratin 8 and 18 (K8/K18) mutations are shown to be associated with a predisposition to liver disease, particularly noncryptogenic liver disease. Unique K8/K18 mutations are shown in patients with diseases including biliary atresia, acute fulminant hepatitis, viral hepatitis B or C, alcoholic liver disease, primary biliary cirrhosis, autoimmune hepatitis, and the like. Livers with keratin mutations had increased incidence of cytoplasmic filamentous deposits. Therefore, K8/K18 are susceptibility genes for developing cryptogenic and noncryptogenic forms of liver disease. Alleles are associated with disease susceptibility, and their detection is used in the diagnosis of a predisposition to these conditions.

The invention also provides methods for the identification of compounds that modulate the expression of genes or the activity or the cellular organization of gene products involved in liver disease, as well as methods for the treatment of liver disease, which may involve the administration of such compounds to individuals exhibiting liver disease symptoms or tendencies.

Figure 2:
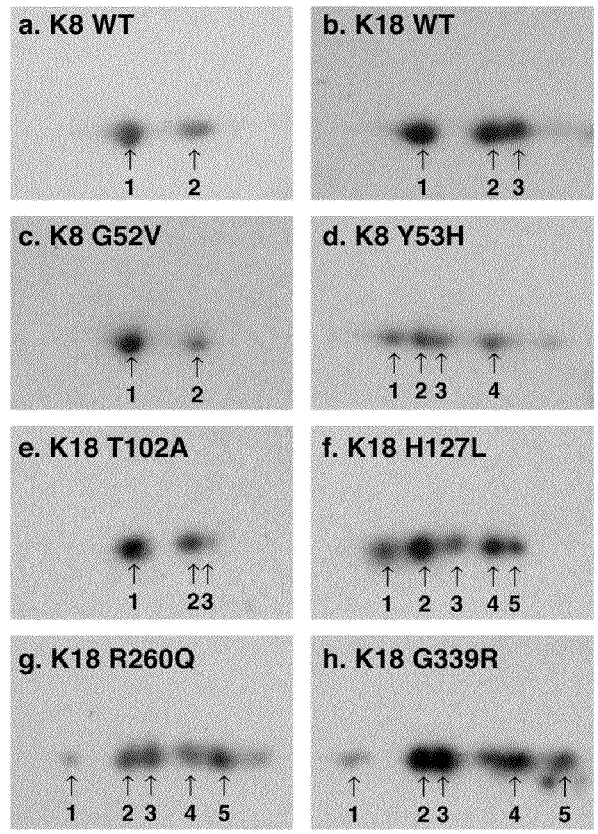
FIGS. 2A-2B: Protein expression of mutant K8 and K18 in explanted livers. (A): K8/K18 immunoprecipitates were obtained from 1% Empigen-solubilized normal liver or livers with keratin mutation. The immunoprecipitates were separated by isoelectic focusing followed by SDS-PAGE, then immunoblotting with anti-K8/K18 antibodies. Note that K8 and K18 in normal liver consist of two or three isoforms depending on their phosphorylation levels (a, b). In contrast, some of the mutant keratins contain four (K8) or five (K18) isoforms due to coexpression of the wild-type and mutant keratin with subsequent generation of altered charged species that have a slightly different mutation-induced isoelectric focusing point (d, f, g, h). (B): K8/K18 immunoprecipitates were prepared from normal liver or liver with the K18 T102A mutation, then analyzed by SDS-PAGE. The K18 bands were cut out, digested with trypsin, then analyzed with a MALDI-TOF mass spectrometer. Note that a peak position at 818.3 was detected only in the liver specimen with the K18 T102A mutation but not in normal liver. The mass difference of 30, between the wild-type and T102A K18 tryptic peptides (848.3 versus 818.3), corresponds to the HO—C—H species (two hydrogen, one oxygen and one carbon atoms with a mass of 30 daltons) that are present in threonine (the wild-type residue) but not in alanine (the mutant residue).
Figure 2:
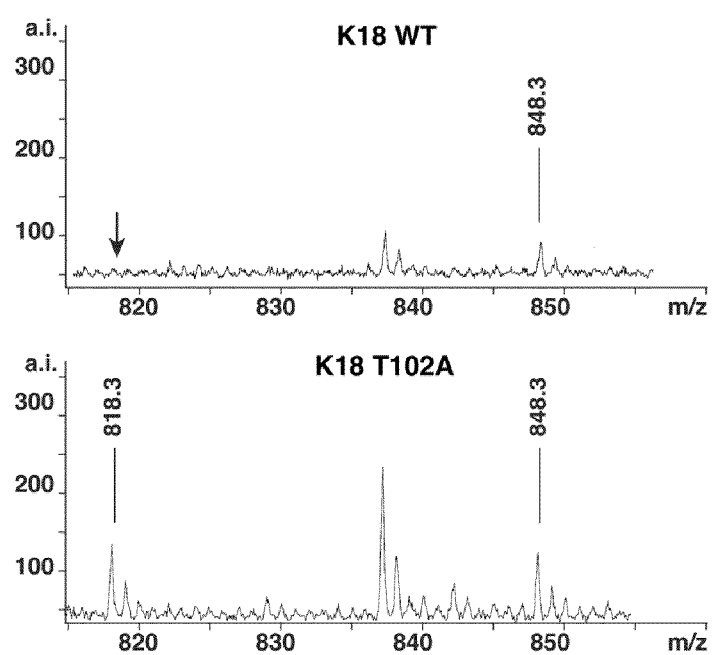
Figure 3:
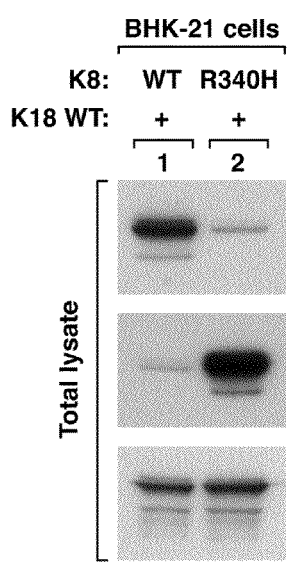
FIGS. 3A-3C: K8 R340H mutation-proximal comparison of type II keratin sequences and confirmation of K8 R340H mutant protein expression in explanted livers. (A) (SEQ ID NO:9) Single letter abbreviations are used to represent amino acids. Bold dots represent amino acids that are identical to the K8 sequence. The shaded area highlights the conserved R340 of K8 and shows the histidine mutation we identified. Note that the K8 R340-containing motif (AEQRG; SEQ ID NO:9, residues 4-8) is highly conserved in type II keratins. It is also conserved across species, being found in mouse and frog K8. (B) BHK cells were transiently cotransfected with K8/K18 WT or K8 R340H/K18 WT. K8/K18 immunoprecipitates were obtained from 1% NP40-solubilized cell lysates. The immunoprecipitates were analyzed by SDS-PAGE, followed by immunoblotting with anti-K8 R340 or anti-K8 H340 epitope-specific antibodies that preferentially recognized K8 WT or K8 R340H mutant, respectively. (C) K8/K18 immunoprecipitates were obtained from 1% NP40-solubilized normal liver or livers with the K8 R340H mutation. Samples were analyzed as described in panel B. Note that anti-K8 R340 (WT) recognizes K8 in the control patient (with K8 WT) and the patient with K8 R340H (lanes 1-6), whereas anti-K8 H340 (mutant) recognizes only patient livers with the K8 R340H mutation (lanes 2-6) but not the normal liver (lane 1). This indicates that the patients with K8 R340H mutation are heterozygous with regard to the keratin mutation. Arrowheads correspond to degraded K8.
Figure 3:
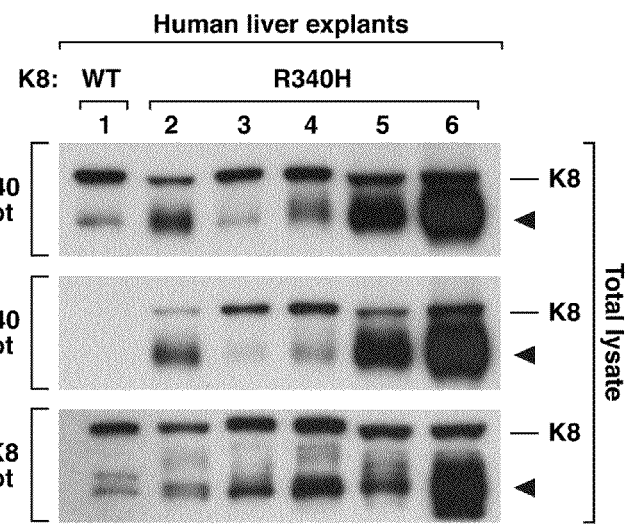
Figure 5:
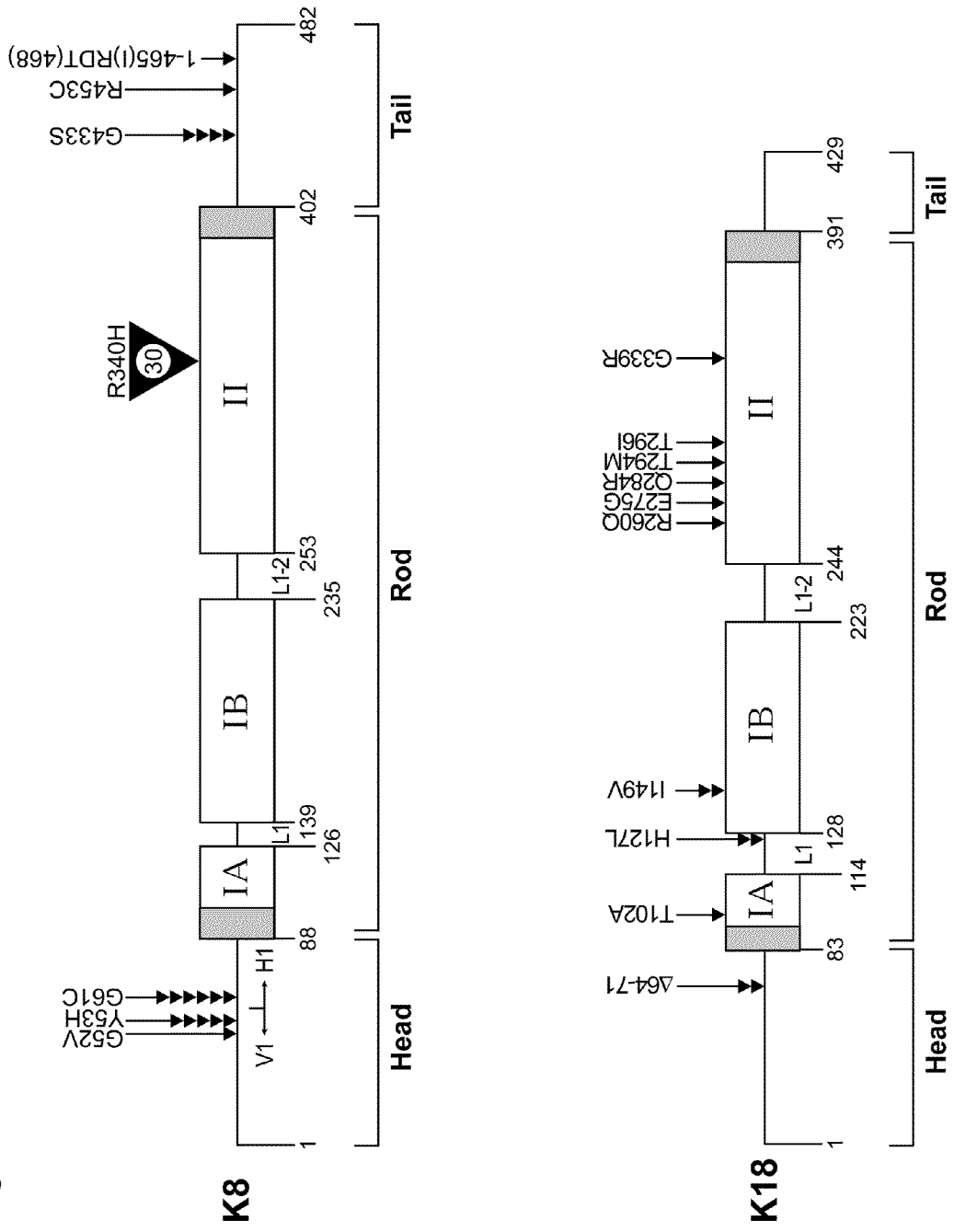
FIG. 5: Distribution of K8 and K18 mutations within the keratin protein backbone. The H1 and V1 subdomains of the K8 head domain, and the amino acid positions of the K8 and K18 domains/subdomains are indicated. For the K8 head/tail and K18 head/rod domains, each arrowhead represents an independently identified mutation at the indicated residue. The 30 K8 R340H mutations are highlighted with a single large arrowhead. Note that the most common K8/K18 mutation to date is the newly identified K8 R340H (30 of 58, 6.4%), with the next most common mutations being K8 G61C (6 of 58) and K8 Y53H (5 of 58). Three patients had a double mutant (K8 R340H and K18 R260Q, K8 R340H and K18 T102A, K18 I149V and K18 T294M). Shaded areas correspond to "hot spots" of epidermal keratin mutations. Note the non-overlap of the location of K8/K18 mutations versus the major location of epidermal keratin mutations.
Figure 6:
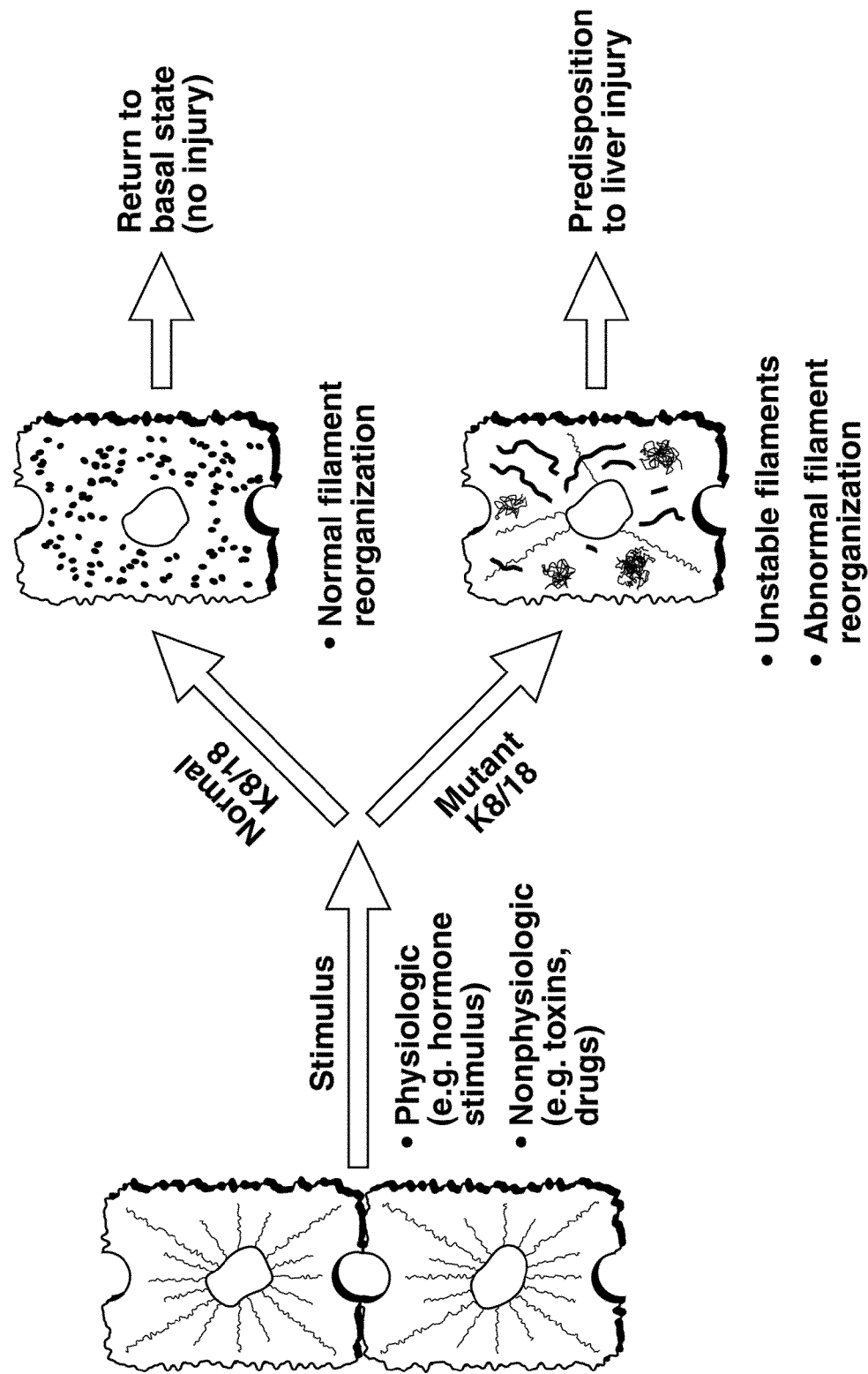
FIG. 6: Schematic model of the effect of keratin mutations on filament organization and subsequent liver injury: Hepatocytes contain an extended array of filamentous keratin and a small soluble keratin pool. A variety of physiologic and nonphysiologic stimuli may result in reversible keratin filament reorganization. However, in the presence of keratin mutations, the keratin filaments may be unstable (as for the K8 Y53H mutation upon heat stress or exposure to okadaic acid), or may not be able to organize normally (as for the K8 G61C mutation upon oxidative stress; e.g. in the presence of $H_2O_2$). Filament instability and abnormal organization may then predispose to liver injury via a variety of mechanisms that include the role of keratins in apoptosis, cell signaling or protein targeting to subcellular compartment.

The above six figures demonstrate: (i) the presence of the keratin mutations at the protein level (FIGS. 2 and 3), (ii) although immunofluorescence staining is not significantly altered in the livers with keratin mutation as compared to those without keratin mutation (FIG. 4A) there appears to be a unique histologic feature of cytoplasmic filamentous deposits that are observed primarily in livers of patients with keratin mutations, (iii) distribution of K8 and K18 mutations in the keratin protein backbone (FIG. 5) and (iv) schematic model of the effect of keratin mutations on filament organization and subsequent liver injury (FIG. 6).

DETAILED DESCRIPTION OF THE EMBODIMENTS

Methods and compositions are provided for the diagnosis of a predisposition to liver or biliary tract disease, including, without limitation, viral hepatitis, autoimmune liver disease, biliary atresia, alcoholic cirrhosis and other acute or chronic toxic liver injury, cryptogenic cirrhosis, acute fulminant hepatitis, primary sclerosing cholangitis, primary biliary cirrhosis, diseases that are linked with cryptogenic cirrhosis, such as nonalcoholic steatohepatitis, and the like. The invention is based, in part, on the evaluation of the K8/K18 keratin genotype, for which alleles predisposing to disease are herein identified. This permits the definition of disease pathways and the identification of a target in the pathway that is useful diagnostically, in drug screening, and therapeutically.

In one aspect of the present invention, methods are provided for determining a predisposition to liver disease in an individual. The methods comprise an analysis of genomic DNA in an individual for an allele of keratin K8 or K18 that confers an increased susceptibility to liver disease. Individuals are screened by analyzing their genomic K8 and/or K18 gene sequence in blood or tissue/cell specimen for the presence of a predisposing allele, as compared to a normal sequence. Screening for the presence of the mutation can also be done using antibodies that specifically identify the keratin mutation, or screening of genomic material in serum.

In addition to the provided sequence polymorphisms, the effect of a candidate polymorphism in a K8 or K18 sequence can be determined for association with a predisposition to liver disease. The candidate polymorphism may be analyzed, for example, for segregation of the sequence polymorphism with the disease phenotype. A predisposing mutation will segregate with incidence of the disease. Alternatively, biochemical studies may be performed to determine whether a candidate polymorphism affects the quantity or quality (in terms of its distribution, interaction with binding partners, etc), or function of the protein.

Intermediate filaments (IFs) are a structurally related family of cellular proteins that are intimately involved with the cytoskeleton. The common structural motif shared by all IFs is a central alpha-helical 'rod domain' flanked by variable N- and C-terminal domains. The rod domain, the canonical feature of IFs, has been highly conserved during evolution. The variable terminals, however, have allowed the known IFs to be classified into 6 distinct types by virtue of their differing amino acid sequences. Keratins compose types I and II IFs. Type I and type II keratins are usually expressed as preferential pairs, in equal proportions in cells, of type I and type II keratins.

Human keratin 18 is a type I IF protein subunit, whose expression is restricted in adults to a variety of so-called "simple-type" epithelial tissues. KRT18 is highly divergent among the type I keratins with N-terminal and C-terminal domains that are quite different from those of epidermal keratins. The KRT18 gene is 3,791 by long and the keratin 18 protein is coded for by 7 exons. The genetic sequence of K18 may be found in Genbank, accession no. NM_000224. The exon structure of KRT18 has been conserved compared to that of other keratin genes, with the exception of a single 3-prime terminal exon that codes for the tail domain of the protein that is represented by 2 exons in epidermal keratins. Keratin 8 is a type II keratin, which is co-expressed with K18. The genetic sequence of K8 may be found in Genbank, accession no. NM_002273.

Mutations in K8 that are associated with a predisposition to liver disease (all the amino acid numbers represent amino acids of the processed protein) include G52V (GGC→GTC); Y53H (TAT→CAT); G61C (GGC→TGC); R340H (CGT→CAT); G433S (GGC→AGC); R453C (CGC→TGC); 1-465(I) RDT(468) (frameshift). The K8 frameshift mutation at Ile-465 generates a truncated 468 (instead of 482) amino acid protein that contains amino acids 1-465, and three additional new amino acids (RDT) after the frameshift mutation. Mutations in K18 that are involved with a predisposition to liver disease include Δ64-71(TGIAG-GLA) (deletion); T102A (ACC→GCC); H127L (CAT→CTT); I149V (ATC→GTC); R260Q (CGG→CAG); E275G (GAG→GGG); Q284R (CAG→CGG); T294M (ACG→ATG); T296I (ACA→ATA); G339R (GGG→AGG). The K18 N-terminal domain deletion (Δ64-71) generated a 421 (instead of 429) amino acid protein (see Table 3).

Keratin K8 or K18 mutations that result in an amino acid substitution or deletion at any one of the mutated positions designated above may be generally defined to include K8 G52X; Y53X; G61X; R340X; G433X; R453X and K18 T102X; H127X; I149X; R260X; E275X; Q284X; T294X; T296X; G339X, where X is any amino acid other than the naturally occurring amino acid as set forth in the published sequence of K8 or K18, and X may also refer to a deleted amino acid or amino acids. Mutations may also be specified in terms of the DNA sequence, and could include any deletions (in addition to those described above), or mutations in the promoter or other regulatory regions that may affect RNA levels or stability under basal conditions or in response to any type of mechanical or nonmechanical stress that the liver may be exposed to due to internal or external factors.

DNA encoding a K8/K18 protein may be cDNA or genomic DNA or a fragment thereof that encompasses one or more of the above identified polymorphisms. As known in the art, cDNA sequences have the arrangement of exons found in processed mRNA, forming a continuous open reading frame, while genomic sequences may have introns interrupting the open reading frame. The term K8/K18 gene shall be intended to mean the open reading frame encoding such specific polypeptides, as well as adjacent 5' and 3' non-coding nucleotide sequences involved in the regulation of expression, up to about 1 kb beyond the coding region, in either direction.

The nucleic acid compositions of the subject invention encode all, none, or a part of a K8 or K18 polypeptide comprising a polymorphism as described above. Fragments may be obtained of the DNA sequence, or of the mRNA, by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The subject K8/K18 genes are isolated and obtained in substantial purity, generally as other than an intact mammalian chromosome. Usually, the DNA will be obtained substantially free of other nucleic acid sequences that do not include a K8/K18 sequence or fragment thereof, generally being at least about 50%, usually at least about 90% pure and are typically "recombinant", i.e. flanked by one or more nucleotides with which it is not normally associated on a naturally occurring chromosome. The subject nucleic acids may be used to identify expression of the gene in a biological specimen.

A number of methods may be used for determining the presence of a predisposing mutation in an individual. Genomic DNA may be isolated from the individual or individuals that are to be tested. DNA can be isolated from any nucleated cellular source such as blood, hair shafts, saliva, mucous, biopsy, feces, etc. mRNA may also be reverse transcribed depending on the detection method. Methods using PCR amplification can be performed on the DNA from a single cell, although it is convenient to use at least about $10^5$ cells. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki et al. (1985) Science 239:487, and a review of current techniques may be found in McPherson et al. (2000) PCR (Basics: From Background to Bench) Springer Verlag; ISBN: 0387916008. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4', 5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the K8/K18 genomic sequence using conventional criteria for selection. The primers in a pair will hybridize to opposite strands, and will collectively flank the region of interest. The primers will hybridize to the complementary sequence under stringent conditions, and will generally be at least about 16 nt in length, and may be 20, 25 or 30 nucleotides in length. The primers will be selected to amplify the specific region of the K8/K18 gene suspected of containing the predisposing mutation. Multiplex amplification may be performed in which several sets of primers are combined in the same reaction tube, in order to analyze multiple exons/introns/promoter and other regulatory regions simultaneously. Each primer may be conjugated to a different label.

After amplification, the products may be size fractionated and evaluated for sequence polymorphisms. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59-74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98-111. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices is used to detect conformational changes created by DNA sequence variation as alterations in electrophoretic mobility or via HPLC type analysis (eg WAVE® System). The hybridization pattern of a control and variant sequence to an array of oligonucleotide probes immobilized on a microarray, may also be used as a means of detecting the presence of variant sequences.

The presence of a predisposing mutation is indicative that an individual is at increased risk of developing liver disease. The diagnosis of a disease predisposition allows the affected individual to seek early treatment, dietary measures, to avoid activities that increase risk for liver disease, and the like.

In addition to genetic tests, the presence of the mutated polypeptide may be detected, by determination of the presence of polypeptide comprising the mutation using analytic methods such as mass spectrometry or immune-related methods such as mutant-specific antibodies, or by detecting the presence of cytoplasmic filamentous deposits.

In a typical assay, a liver sample is assayed for the presence of K8 and/or K18 specific sequences by combining the sample with a K8 and/or K18 specific binding member, and detecting directly or indirectly the presence of the complex formed between the two members. The term "specific binding member" as used herein refers to a member of a specific binding pair, i.e. two molecules where one of the molecules through chemical or physical means specifically binds to the other molecule. In this particular case one of the molecules is K8 and/or K18, where K8 and/or K18 is any protein substantially similar to the amino acid sequence of the human polypeptide sequences of this family, as described above, or a epitope containing fragment thereof, and further comprising a predisposing mutation. The complementary members of a specific binding pair are sometimes referred to as a ligand and receptor. Testing can also be done using any source of genomic material from a given individual or any tissue that also expresses K8 and K18 (eg gastric, small or large intestinal biopsy).

In the present specification and claims, the term "polypeptide fragments", or variants thereof, denotes both short peptides with a length of at least two amino acid residues and at most 10 amino acid residues, oligopeptides with a length of at least 11 amino acid residues, 20 amino acid residues, 50 amino acid residues, and up to about 100 amino acid residues; and longer peptides of greater than 100 amino acid residues up to the complete length of the native polypeptide.

Polypeptides detected by the present methods include naturally occurring alpha and beta subunits, as well as variants that are encoded by DNA sequences that are substantially homologous to one or more of the DNA sequences specifically recited herein, for example variants having at least 80%, 85%, 90%, 91%, 92%, 93%, 94%, 95%, 96%, 97%, 98%, 99%, or 99.5% sequence identity. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Alternatively, monoclonal or polyclonal antibodies are raised to K8 and/or K18 polypeptides comprising a predisposing mutation. The antibodies may be produced in accordance with conventional ways, immunization of a mammalian host, e.g. mouse, rat, guinea pig, cat, rabbit, dog, etc., fusion of resulting splenocytes with a fusion partner for immortalization and screening for antibodies having the desired affinity to provide monoclonal antibodies having a particular specificity. These antibodies can be used for affinity chromatography, ELISA, RIA, and the like. The antibodies may be labeled with radioisotopes, enzymes, fluorescers, chemiluminescers, or other label, which will allow for detection of complex formation between the labeled antibody and its complementary epitope. Generally the amount of bound K8 and/or K18 detected will be compared to negative control samples from normal tissue or cells.

Screening assays identify compounds that modulate the expression or structure of K8/K18. Such compounds may include, but are not limited to peptides, antibodies, or small organic or inorganic compounds. Methods for the identification of such compounds are described below.

Cell- and animal-based systems can act as models for liver disease and are useful in such drug screening. The animal- and cell-based models may be used to identify drugs, pharmaceuticals, therapies and interventions that are effective in treating liver disease. In addition, such animal models may be used to determine the $LD_{50}$ and the $ED_{50}$ in animal subjects, and such data can be used to determine the in vivo efficacy of potential liver disease treatments. Animal-based model systems of liver disease may include, but are not limited to, non-recombinant and engineered transgenic animals. Animal models exhibiting liver disease symptoms may be engineered by utilizing, for example, K8 and/or K18 gene sequences in conjunction with techniques for producing transgenic animals that are well known to those of skill in the art. For example, target gene sequences may be introduced into, and knocked out or overexpressed in the genome of the animal of interest. Animals of any species, including, but not limited to, mice, rats, rabbits, guinea pigs, pigs, micro-pigs, goats, and non-human primates, e.g., baboons, monkeys, and chimpanzees may be used to generate liver disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313-321); electroporation of embryos (Lo, 1983, Mol. Cell. Biol. 3:1803-1814); and sperm-mediated gene transfer (Lavitrano et al., 1989, Cell 57:717-723); etc.

Specific cell types within the animals may be analyzed and assayed for cellular phenotypes characteristic of liver disease. Further, such cellular phenotypes may include a particular cell type's fingerprint pattern of expression as compared to known fingerprint expression profiles of the particular cell type in animals exhibiting liver disease symptoms.

Cells that contain and express K8/K18 can be utilized to identify compounds that exhibit pharmacologic activity of interest, in the prevention of liver disease. Cells of a cell type known to be involved in liver disease may be transfected with sequences capable of increasing or decreasing the amount of K8 and/or K18 gene expression within the cell. For example, K8/K18 gene sequences may be introduced into, and overexpressed in, the genome of the cell of interest, or, if endogenous target gene sequences are present, they may be either overexpressed or, alternatively disrupted in order to underexpress or inactivate target gene expression.

Transfection of target gene sequence nucleic acid may be accomplished by utilizing standard techniques. Transfected cells can be evaluated for the presence of the recombinant K8/K18 gene sequences, for expression and accumulation of K8/K18 gene mRNA, and for the presence of recombinant K8/K18 protein. Where a decrease in K8/K18 gene expression is desired, standard techniques may be used to demonstrate whether a decrease in expression is achieved.

In vitro systems may be designed to identify compounds capable of preventing or treating liver disease. Such compounds may include, but are not limited to, peptides made of D- and/or L-configuration amino acids, phosphopeptides, antibodies, and synthetic or natural small organic or inorganic molecules. For example, assays may be used to identify compounds that improve liver function involves preparing a reaction mixture of K8/K18 and a test compound under conditions and for a time sufficient to allow the two components to interact, and detecting the resulting change in the polypeptide structure. Alternatively, a simple binding assay can be used as an initial screening method. These assays can be conducted in a variety of ways. For example, one method to conduct such an assay would involve anchoring K8/K18 protein or a test substance onto a solid phase and detecting complexes anchored on the solid phase at the end of the reaction. In another embodiment of such a method, the assay tests the presence of products modulated by K8/K18.

In a binding assay, the reaction can be performed on a solid phase or in liquid phase. In a solid phase assay, the nonimmobilized component is added to the coated surface containing the anchored component. After the reaction is complete, unreacted components are removed under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a binding reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Cell-based systems such as those described above may be used to identify compounds that act to ameliorate liver disease symptoms. For example, such cell systems may be exposed to a test compound at a sufficient concentration and for a time sufficient to elicit such an amelioration of liver disease symptoms in the exposed cells. After exposure, the cells are examined to determine whether one or more of the liver disease cellular phenotypes has been altered to resemble a more normal or more wild type, non-liver disease phenotype. Liver disease "symptoms" in cells include surrogate markers such as changes in keratin filament organization, keratin properties (such as phosphorylation or solubility), or interaction with a binding partner.

In addition, animal-based disease systems, such as those described, above may be used to identify compounds capable of ameliorating disease symptoms. Such animal models may be used as test substrates for the identification of drugs, pharmaceuticals, therapies, and interventions, which may be effective in treating or preventing disease. For example, animal models may be exposed to a compound, suspected of exhibiting an ability to ameliorate liver disease symptoms, at a sufficient concentration and for a time sufficient to elicit such an amelioration of disease symptoms in the exposed animals. The response of the animals to the exposure may be monitored by assessing the reversal of disorders associated with disease.

With regard to intervention, any treatments that reverse any aspect of liver disease symptoms may be considered as candidates for human disease therapeutic intervention. Dosages of test agents may be determined by deriving dose-response curves.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The methods described herein may be performed, for example, by utilizing pre-packaged diagnostic kits comprising at least one specific K8/K18 nucleic acid reagent described herein, which may be conveniently used, e.g., in clinical settings, for prognosis of patients susceptible to liver disease.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

EXPERIMENTAL

Methods

Patients: We included for the analysis specimens of 467 explanted livers that were obtained from the liver transplantation units at Stanford University, the University of California San Francisco, and California Pacific Medical Center. The 467 liver samples were previously examined for K8/K18 mutations in 5 exonic regions (Ku et al, N. Engl. J. Med. 344:1580-1587, 2001 and Ku et al, Proc. Natl. Acad. Sci. USA. 100:6063-6068, 2003), that included the epidermal keratin domains where most of the mutations have been identified (Irvine & McLean, Br. J. Dermatol. 140:815-828, 1999). Subsequent to this, the frequency of K8/K18 mutations were determined in the remaining 10 exons of K8/K18. Peripheral blood samples from 349 healthy volunteers were obtained from the Stanford Blood Bank and used for genomic DNA isolation. In addition and when available, blood samples were obtained from patients with the identified keratin mutations and/or from their children or parents. The patients' sex and racial/ethnic background were determined from patients' medical records. No information could be found on 15 patients due to lack of records or to retransplant.

For the control samples, anonymous information regarding sex and race was provided by the Stanford Blood Bank. The diagnoses were based on the United Network for Organ Sharing transplant listing. Medical records of all patients with a keratin mutation were reviewed and the diagnosis was confirmed.

Histopathology and statistical analysis: Pathology slides from the explanted livers with keratin mutations, and matched liver disease controls, were reviewed by a single pathologist who did not know which specimens harbored the keratin mutations. Slides from the explanted livers of all 17 patients with keratin mutations, as well as disease-matched controls, were examined and scored for the presence or absence of features including Mallory and acidophil bodies, cell size, ground glass cytoplasm, and dysplasia. Images of the hematoxylin and eosin stained liver sections were obtained using a Nikon Eclipse E1000 microscope with a 40× objective. Data analysis was conducted using the Fisher's exact test performed with Statistical Analyzing System software (SAS).

Figure 1:
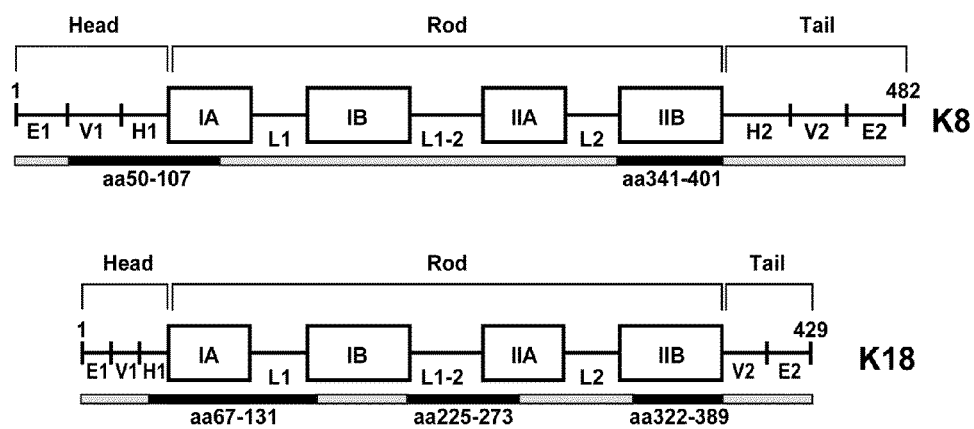
FIGS. 1A-1B: Protein domains analyzed for K8/K18 mutations and an example of the identification of a K8 mutation. (A) A central rod domain, consisting of α-helical subdomains, is flanked by non-α-helical head/tail domains. The head/tail domains are further subdivided into E, V and H regions. The subdomains of the rod are connected by nonhelical linker (L1, L1-2, L2) regions. The amino acid (aa) regions in black bars represent 5 domains that were examined for K8/K18 mutations. The remaining regions in gray bars contain 10 exonic K8/K18 domains that have been analyzed for mutations. (B) PCR products, from a control patient (with K8 WT) and a patient with K8 R340H, were analyzed by denaturing HPLC using a WAVE® System. The control (K8 WT; SEQ ID NO:5, SEQ ID NO:6) is characterized by one major peak, while the K8 R340H; SEQ ID NO:7, SEQ ID NO:8 shows a different chromatogram due to resolution of the homoduplexes from the heteroduplexes, thereby suggesting the presence of a K8 mutation. Electropherograms from DNA sequencing confirm the presence of a K8 R340H heterozygous missense mutation (CGT→CAT).
Figure 1:
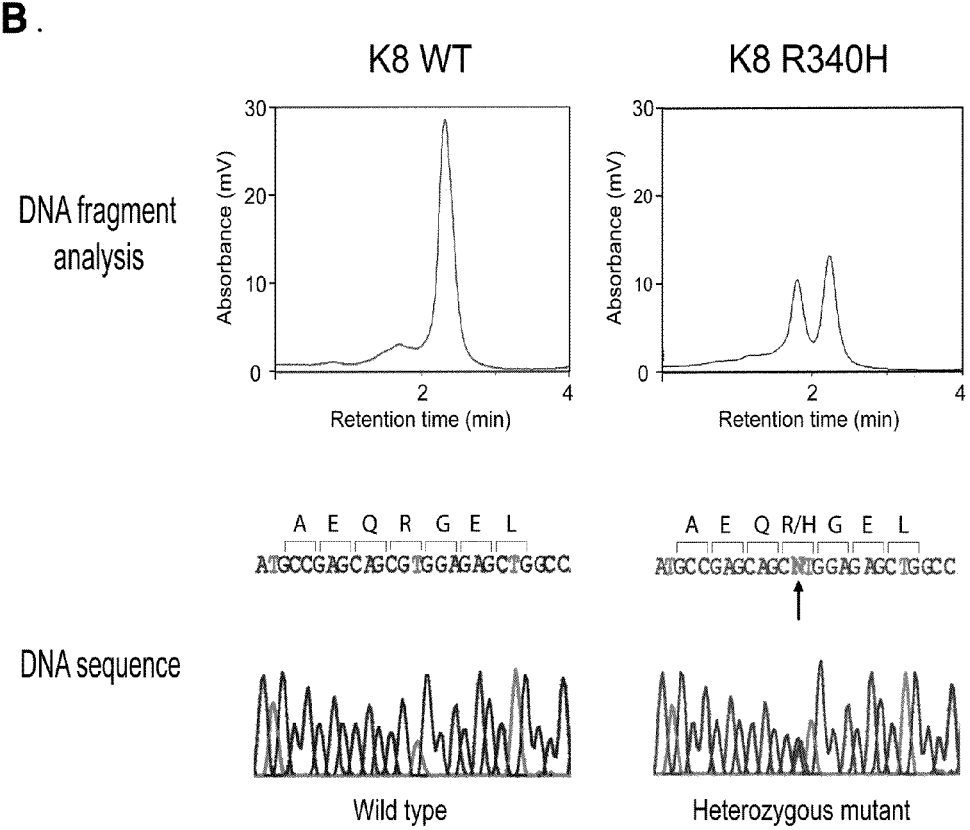

Molecular methods: Genomic DNA was prepared using a Dneasy tissue kit (QIAGEN Inc., Chatsworth, Calif.). Exonic regions (FIG. 1A) were amplified by the polymerase chain reaction. The amplified products were analyzed for mutation using the WAVE® System (Transgenomic Inc, San Jose, Calif.), and any samples with a "shift" pattern suggestive of a mutation were sequenced in the forward and reverse directions to confirm the presence of a mutation (FIG. 1B).

Biochemical methods: Tissues were homogenized in phosphate buffered saline containing 1% n-dodecyl-N,N-dimethylglycine (Empigen BB, Calbiochem-Novabiochem, San Diego, Calif.), 5 mM EDTA, and protease inhibitors. Homogenized samples were solubilized for 30 minutes, pelleted then used for immunoprecipitation of K8/K18. Precipitates were analyzed by: (i) SDS polyacrylamide gel electrophoresis (PAGE), under reducing or non-reducing conditions, then Coomassie staining, (ii) SDS-PAGE then immunoblotting, or (iii) two-dimensional gels using isoelectric focusing (horizontal direction) and SDS-PAGE (vertical direction) then immunoblotting.

Mass spectrometry analysis: Separated K8 and K18 bands were cut out from preparative gels, reduced with dithiothreitol, alkylated with iodoacetamide, and then digested with trypsin in 50 mM ammonium bicarbonate (pH 7.8) using a standard in-gel-digestion procedure. Extracted K8 or K18 tryptic peptides were desalted using a C18 ZipTip (Millipore, Mass.) then eluted with 50% acetonitrile-0.1% trifluoroacetic acid (TFA). A 1 µl aliquot of the eluant was mixed with equal volume of matrix solution (saturated a-cyano-4-hydroxycinnamic acid in 0.1% TFA-50% acetonitrile in water) and analyzed by a MALDI-TOF mass spectrometer (Bruker Biflex III) equipped with a nitrogen 337 nm laser. The mass spectra were acquired in the reflectron mode. Internal mass calibration was performed with two trypsin autodigested fragments (842.5 and 2211.1 Da). K8 tryptic peptides were also digested with CNBr and similarly analyzed.

Antibody generation: Two polyclonal antibodies were generated after immunizing rabbits with synthetic peptides containing wild type K8 R340 ($^{335}$ADAEQRGELAI) or mutant K8 H340 ($^{335}$ADAEQHGELAI). As shown in FIG. 2B, anti-K8 R340 or anti-K8 H340 antibody recognized predominantly K8 WT or the K8 R340H mutant, respectively, that were co-expressed in transfected BHK cells with wild type K18.

Immunofluorescence staining: Snap-frozen liver explants were embedded in optimum cutting temperature compound, sectioned then fixed in acetone (−20° C., 10 min). Sections were double stained with antibodies directed to K8/K18 (13) or vimentin (NeoMarkers, Freemont, Calif.). Flourescence images were obtained using an MRC 1024ES confocal scanner (BioRad, Hercules, Calif.) coupled to a Nikon Eclipse TE300 microscope.

Results

Identification of K8 and K18 mutations: We tested DNA extracted from liver explants or peripheral blood for the presence of K8 or K18 mutations. Two cohorts were examined, whose demographics are summarized in Table 1: a group of 467 patients with a variety of liver diseases, and a control group of 349 blood bank donors. The ethnic background of the two cohorts was generally similar except for a higher preponderance of Caucasian patients in the control group.

TABLE 1

Racial/Ethnic Background and Sex of Patients and Controls

| Charactertics | Liver Disease | Patients | Blood Bank | Controls |
|---|---|---|---|---|
| White | 274 | 58.6% | 268 | 76.8% |
| Male | 139 | | 154 | |
| Female | 135 | | 114 | |
| Black | 26 | 5.6% | 9 | 2.6% |
| Male | 9 | | 5 | |
| Female | 17 | | 4 | |
| Hispanic | 67 | 14.3% | 42 | 12.0% |
| Male | 28 | | 21 | |
| Female | 39 | | 21 | |
| Asian/Pacific Islander | 57 | 12.1% | 23 | 6.6% |
| Male | 36 | | 12 | |
| Female | 21 | | 11 | |
| Middle Eastern/Indian | 20 | 4.2% | 6 | 1.7% |
| Male | 14 | | 2 | |
| Female | 6 | | 4 | |
| Native American | 2 | 0.8% | 1 | 0.30% |
| Male | 1 | | 0 | |
| Female | 1 | | 1 | |
| Unknown | 21 | 4.4% | 0 | 0% |
| Total | 467 | | 349 | |

The etiology of the liver diseases is broad (Table 2), most of which is noncryptogenic (based on clinical criteria, 68 of the 467 patients were classified as having cryptogenic liver disease; Table 2). We included the control blood bank cohort in order to address which mutations identified in the liver disease cohort are likely to represent "true" mutations versus polymorphism variants found in the general population. We previously reported that 7 heterozyous missense mutations in 5 exonic regions of K8/K18 were identified in 17 of 467 liver disease patients and 2 of 349 blood bank controls (3.6% and 0.6% frequency; p<0.004) (Ku et al, Proc Natl Acad Sci USA. 100:6063-6068, 2003). The 5 exonic regions included the epidermal keratin domains where most of the mutations have been identified in skin disease patients.

TABLE 2

Liver Disease Etiologies and Frequency of Keratin Mutations

| Etiology of Liver Disease | # of Patients (# with keratin mutations) | % Keratin Mutations |
|---|---|---|
| Hepatitis C | 80 (9) | 11.2 |
| Hepatitis C/Alcohol | 28 (5) | 17.8 |
| Hepatitis B | 44 (5) | 11.4 |
| Biliary Atresia | 47 (3) | 6.4 |
| Alcohol | 33 (3) | 9.1 |
| Cryptogenic | 68 (7) | 10.3 |
| Primary Biliary Cirrhosis | 12 (4)† | 33.3 |
| Primary Sclerosing Cholangitis | 15 (1) | 6.7 |
| Acute Fulminant Hepatitis | 35 (4)† | 11.4 |

TABLE 2-continued

Liver Disease Etiologies and Frequency of Keratin Mutations

| Etiology of Liver Disease | # of Patients (# with keratin mutations) | % Keratin Mutations |
|---|---|---|
| Neonatal Hepatitis | 9 (2) | 22.7 |
| Autoimmune Hepatitis | 33 (2) | 6.1 |
| Metabolic/Genetic* | 23 | 8.7 |
| Cystic Fibrosis | (1) | |
| Metabolic/other | (1) | |
| Primary Liver Cancer** | 5 (0) | |
| Drug Induced Liver Failure | 9 (1) | 11.1 |
| Other§ | 26 (10)† | 38.5 |
| Total | 467 (58) | 12.4 |

*Metabolic/genetic diagnoses included 4 Wilson's disease, 3 hemochromatosis, 3 α1-antitrypsin deficiency, 2 cystic fibrosis, 3 primary oxalosis, 1 Crigler-Najjar, 1 ornithine transcarbamoylase deficiency, 1 Nieman-Pick, 1 arginosuccinicaciduria, 1 tyrosinemia, 1 citrolemia, 1 glycogen storage, and 1 "Metabolic disease" that is unclassified.
**Patients with viral hepatitis and hepatoma were included under the appropriate viral hepatitis category. Primary liver cancers included 1 hepatoma, 3 hemangioendotheliomas, and 1 hepatosarcoma.
†One patient with primary biliary cirrhosis had a double mutant (K8 R340H and K18 R260Q), one patient with acute fulminant hepatitis had a double mutant (K8 R340H and K18 T102A), and one patient with unknown liver disease etiology had a double mutant (K18 I149V and K18 T294M). All other patient had a single mutation.
§The "Other" category of liver diseases included Budd-Chiari, hepatic artery thrombosis, polycystic disease, Caroli's disease, Byler's disease, 2 chronic rejection, primary graft nonfunction, Klatskin tumor, parenteral nutrition-induced, carcinoid, hepatitis B and C, hepatitis B and alcohol, multiple adenomas, secondary biliary cirrhosis, veno-occlusive disease, and congenital hepatic fibrosis. At least 11 of the patients screened had received a priori orthotopic liver transplant. For a few patients, their disease etiology could not be discerned from the medical records.

TABLE 3

K8/ K18 Mutation in Human Liver Diseases

| | Mutations | | # of mutation carriers from | |
|---|---|---|---|---|
| | | | Liver disease cohort (467) | Blood bank controls (349) |
| | Amino Acid SEQ ID NO: 4 | Nucleotide SEQ ID NO: 3 | | |
| K8 | G52V | GGC→GTC | 1 | None |
| | Y53H | TAT→CAT | 5 | 1 |
| | G61C | GGC→TGC | 6 | 1 |
| | R340H | CGT→CAT | 30 | 10 |
| | G433S | GGC→AGC | 4 | 1 |
| | R453C | CGC→TGC | 1 | None |
| | I-465(I) RDT(468) | Frameshift | 1 | None |
| | I62V* | ATC→GTC | 1 | 7 |
| | L71L** | CTG→CTA | 1 | None |
| | A318S* | GCT→TCT | 5 | 2 |
| | R301C* | CGC→TGC | None | 1 |
| | E376E** | GAG→GAA | 2 | — |
| | V460M* | GTG→ATG | None | 1 |
| | V479I* | GTC→ATC | None | 2 |
| | Amino Acid | Nucleotide | | |
| | SEQ ID NO: 2 | SEQ ID NO: 1 | | |
| K18 | Δ 64-71 (TGIAGGLA) | Deletion | 2 | None |
| | T102A | ACC→GCC | 1 | None |
| | H127L | CAT→CTT | 2 | None |
| | I149V | ATC→GTC | 2 | None |
| | R260Q | CGG→CAG | 1 | None |
| | E275G | GAG→GGG | 1 | None |
| | Q284R | CAC→CGG | 1 | None |
| | T294M | ACG→ATG | 1 | None |
| | T296I | ACA→ATA | 1 | None |
| | G339R | GGG→AGG | 1 | None |
| | S229T* | AGC→ACC | 2 | 4 |
| | Y330Y** | TAC→TAT | 1 | None |
| K8 | | | 48/467 | 13/349 |
| K18 | | | 13/467 | None |
| K8/18 | | | 58†/467 | 13/349 |

Single letter standard abbreviations are used to represent amino acids and nucleotides.
Sequences with bold lettering refer to mutations that pose a potential risk factor for subsequent development of liver disease, based on analysis of the liver disease cohort and the blood bank control group.
Single asterisks (*) highlight amino acid substitutions that are considered polymorphisms since they were found at similar, or higher, incidence in the control cohort as compared with the liver disease group.
Double asterisks (**) highlight "silent" nucleotide mutations that do not result in any amino acid change. The total number of K8/K18 mutations shown represents true mutations and does not include "silent" mutations or polymorphisms.
†Three patients had a double mutant (K8 R340H and K18 R260Q, K8 340H and K18 T102A or K18 I149V and K18 T294M), which results in a total number of patients with keratin mutation of 58 (i.e. 61 − 3 = 58).

More recently, we analyzed the 10 remaining exonic regions for K8/K18 mutations that were not examined previously (manuscript in preparation). Aside from several new polymorphisms, we identified 10 novel K8/K18 amino acid heterozygous mutations (four K8 and six for K18) caused by deletion (1), frameshift (1) and missense alterations (8). The K8 frameshift mutation at Ile-465 generated a truncated 468 (instead of 482) amino acid protein. The K18 N-terminal domain deletion (Δ64-71) generated a 421 (instead of 429) amino acid protein. The new K8/K18 mutations were found in 44 of 467 patients and 11 of 349 controls (Table 3). Three patients had a double mutant. One patient with primary biliary cirrhosis had K8 R340H and K18 R260Q, one patient with acute fulminant hepatitis had K8 R340H and K18 T102A, and one patient with unknown liver disease etiology had K18 I149V and K18 T294M. Combining this recent data with our previous data of all the patients identified with keratin mutations, the most common mutation is K8 R340H (30 of 58, ~52%).

TABLE 4

Liver Disease Etiologies and Frequency of Keratin Mutations

| | Liver Disease Patients | | Blood Bank Controls |
|---|---|---|---|
| Keratin Mutation | Liver Disease | No. with mutation/Ethnicity* | No. with mutation/Ethnicity |
| K8 G52V | Viral Hepatitis | 1/White | none/— |
| K8 Y53H | Viral hepatitis, BA, CC | 5/3 Black, 1 White, 1 Hispanic | 1/Black |
| K8 G61C | Viral Hepatitis, Alcohol, CC, CF | 6/1 Black, 4 White, 1 Unknown | 1 White |
| K8 R340H | Viral Hepatitis, AFH, others | 30/14 White, 10 Hispanic, 1 Indian, 5 Unknown | 10/8 White, 2 Hispanic |

TABLE 4-continued

Liver Disease Etiologies and Frequency of Keratin Mutations

| | | Liver Disease Patients | Blood Bank Controls |
|---|---|---|---|
| Keratin Mutation | Liver Disease | No. with mutation/Ethnicity* | No. with mutation/Ethnicity |
| K8 G433S | Viral Hepatitis, Alcohol, BA | 4/2 Black, 2 Unknown | 1/Black |
| K8 R453C | CCC | 1/Unknown | none/— |
| K8 1-465(I)RDT(468) | PSC | 1/White | none/— |
| K8 Δ 64-71 (TGIAGGLA) | Viral Hepatitis, Alcohol | 2/1 White, 1 Unknown | none/— |
| K8 T102A | AFH | 1/Hispanic | none/— |
| K8 H127L | Metabolic, CC | 2/White | none/— |
| K8 I149V | PBC | 2/1 Hispanic, 1 Unknown | none/— |
| K8 R260Q | PBC | 1/Hispanic | none/— |
| K8 E275G | Viral Hepatitis | 1/White | none/— |
| K8 Q284R | Viral Hepatitis | 1/White | none/— |
| K8 T294M | Unknown | 1/Unknown | none/— |
| K8 T296I | Viral Hepatitis | 1/Asian | none/— |
| K8 G339R | Hepatic Artery Thrombosis | 1/Unknown | none/— |
| Prevalence of Keratin Mutations | | 58**/467 (12.4%)† | 13/349 (3.7%)† |

BA = Biliary Atresia, CC = Cryptogenic Cirrhosis, CF = Cystic Fibrosis, PBC = Primary Biliary Cirrhosis, AFH = Acute Fulminant Hepatitis
PSC = Primary Sclerosing Cholangitis
*The ethnicities and sexes of the 58 liver disease patients with keratin mutations were 26 White (11 female/15 male), 6 Black (4 female/2 male), 12 Hispanic (8 female/4 male), 1 Indian (1 female), 1 Asian (1 male) and 12 unknown.
**Three patients had a double mutation (i.e. these 58 patients are counted only once, see also legend for Table 2). One patient with primary biliary cirrhosis had K8 R340H and K18 R260Q, one patient with acute fulminant hepatitis had K8 R340H and K18 T102A, and one patient with unknown liver disease etiology had K18 I149V and K18 T294M.
†P value <0.0001 (Proportion of patients with keratin mutations from the combined liver disease cohorts compared with blood bank controls).

The mutations that were identified in 58 of 467 patients represent a mutation frequency of 12.4%, as compared with a mutation frequency of 3.7% found in 13 of 349 controls (P<0.0001; Tables 3 and 4). Given the demographics of patients with keratin mutations, there does not appear to be any obvious accumulation of keratin mutations in a particular sex or ethnic background (Table 4). Since most of the specimen that we analyzed consisted of liver explants, we also tested blood specimen for the germline presence and transmission of the identified keratin mutations, in order to exclude the possibility that the mutations we identified occurred during development of disease. Of the 58 independent patients with K8/K18 mutations we were able to locate 4 patients and/or their offspring. All four of these patients and/or their offspring blood specimen had the identical heterozygous keratin mutation to that identified in the diseased explanted liver (Table 5). Therefore, the K8/K18 mutations we identified are not a consequence of the liver disease but, rather, predispose their carriers to subsequent development of liver disease.

TABLE 5

Germline Presence and Transmission of K8/K18 Mutations*

| | | | Mutation in blood of | |
|---|---|---|---|---|
| Keratin mutation | | Liver disease | patients | offspring |
| K8 | Y53H | Hepatitis B | Yes | N.A. |
| | G61C | Cryptogenic | Yes | Yes** (in 3 of 4 tested) |
| | R340H | Idiopathic FHF | Yes | N.A. |
| | R340H | Hepatitis C and alcohol | Yes | N.A.,* |

TABLE 5-continued

Germline Presence and Transmission of K8/K18 Mutations*

| | | | Mutation in blood of | |
|---|---|---|---|---|
| Keratin mutation | | Liver disease | patients | offspring |
| | R340H | Hepatitis C | Yes | Yes** (in 1 of 2 tested) |
| | R340H | Biliary atresia | Yes | N.A. |
| | R340H | Hepatitis B | Yes | N.A. |
| | R340H | Cryptogenic | Yes | N.A. |
| | G433S | Biliary atresia | Yes | N.A. |
| | 1-465(I) RDT(468) | PSC | Yes | N.A. |
| K18 | Δ 64-71 (TGIAGGLA) | Hepatitis C and alcohol | N.A. | Yes (1 tested) |
| | H127L | Cryptogenic | N.A. | Yes (1 tested) |
| | I149V | PSC | Yes | N.A. |
| | R260Q | PBC | Yes | Yes (1 tested) |

FHF = Fulminant hepatic failure, PBC = Primary biliary cirrhosis, PST = Primary sclerosing cholangitis
N.A. = Not available
*All identified mutations are heterozygous.
**One of the tested offspring has wild type K8.

Expression of mutant keratin proteins: We examined, biochemically, the liver explant specimens from some of the mutation carriers within the cohort of 467 patients in order to confirm the presence of the mutation at the protein level. Mutations that were examined included 8 types: K8 G52V/Y53H/G61C/R340H and K18 T102A/H127L/R260Q/G339R (Table 3). The presence of the K8 G61C protein was confirmed as we did previously (Ku et al, N Eng J Med 344:1580-1587, 2001), by formation of K8 dimers (under nonreducing gel conditions) due to the newly introduced cysteine (normally absent in K8/K18). We also used two-dimensional gels to separate proteins based on their charge, and thereby confirmed the presence of the K8 Y53H and K18 H127L/R260Q/G339R species (FIG. 2A) (Ku et al, Proc Natl Acad Sci USA 100:6063-6068, 2003). These four K8/K18 mutations generated proteins with a different charge as compared to their wild-type counterparts, and resulted in new isoforms (4 isoforms instead of 2 for mutant K8, and 5 isoforms instead of 3 for mutant K18, FIG. 2A).

Two-dimensional gel analysis was, however, not informative for mutations that do not significantly alter the isoelectric point (FIG. 2A, K8 G52V and K18 T102A variants). For these mutations, we compared the mass spectrometric profiles of protease-generated fragments of wildtype and mutant keratins and tested for the presence of peptides that have a mutation-altered mass (Ku et al, Proc Natl Acad Sci USA 100:6063-6068, 2003). As shown in FIG. 2B, presence of the K18 T102A protein was confirmed by detection of its alanine-102-containing peptide with a predicted mass of 818.3 (in addition to the wild-type threonine-102-containing peptide with a predicted mass of 848.3). A similar analysis was attempted for K8 G52V but no peptide that corresponds to a valine-to-glycine substitution was detected, likely due to inability to recover it from the isolation column.

Given that the K8 R340H mutation was the most common mutation, found in 30 of 58 affected individuals at the highly conserved K8 R340 (FIG. 3A), we generated and used polyclonal antibodies to examine the presence of wild type K8 versus the mutant K8 R340H protein in patient liver explants. The two antibodies we generated were directed towards the wild type K8 R340 residue ($^{335}$ADAEQRGELAI) or the mutant K8 H340 residue ($^{335}$ADAEQHGELAI). Specificity of the antibodies was tested in transfected cells that expressed K8 WT or K8 R340H. Anti-K8 R340 (i.e. K8 WT) or anti-K8 H340 antibody recognized predominantly K8 WT or the K8 R340H mutant, respectively (FIG. 3B). Expression of the K8 R340H protein in patient liver explants was confirmed by immunoblotting of total explant liver lysates with the antibodies. As shown in FIG. 3C, anti-K8 R340 (WT) recognizes K8 in the control patient and the patients with K8 R340H (lanes 1-6), whereas anti-K8 H340 (mutant) recognizes only patient livers with the K8 R340H mutation (lanes 2-6) but not the normal liver (lane 1). This indicates that the patients with K8 R340H mutation are heterozygous.

Figure 4:
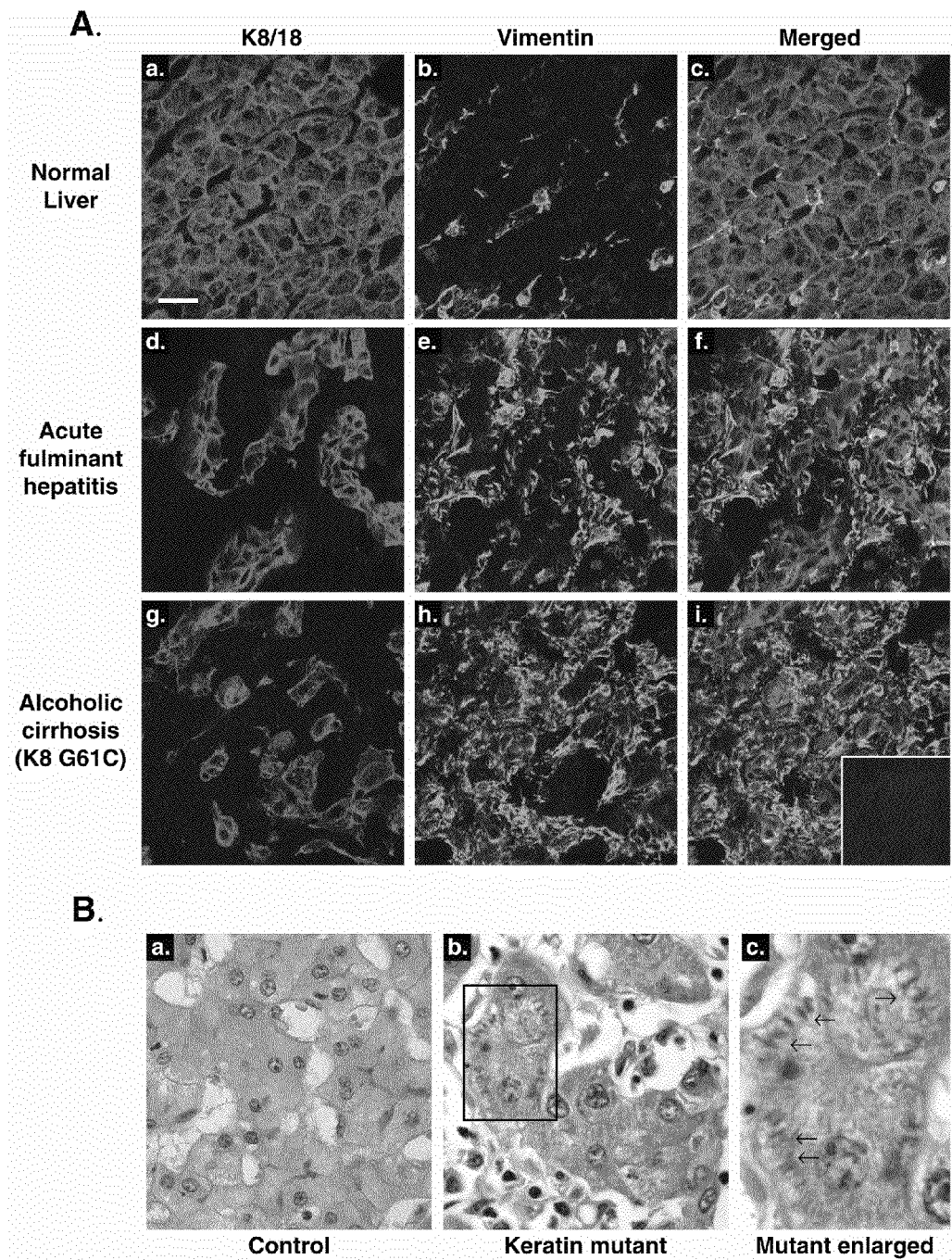
FIGS. 4A-4B: Keratin filament organization in human liver explants, and histologic findings of livers harboring the keratin mutations. (A): Human livers were sectioned, fixed in acetone and double-stained with rabbit anti-K8/18 or mouse anti-vimentin antibodies. Inset in panel i shows control double staining using fluorochrome-conjugated goat anti-rabbit and goat anti-mouse antibodies without adding any primary antibodies. All images were obtained using the same magnification. Bar in panel a=20 µm. (B): Hematoxylin and eosin staining of explanted liver from two patients with acute fulminant hepatitis. Panel "a" is from a patient without a keratin mutation while panel "b" is from a patient with the K18 T102A mutation. The region outlined by a box in "b" is magnified in panel "c" to illustrate the cytoplasmic filamentous deposits noted primarily in livers of patients with keratin mutations.

Effect of keratin filament organization on keratin filament organization and liver histology: We compared keratin filament organization in liver explants of patients with and without keratin mutations (Ku et al, Proc Natl Acad Sci USA 100:6063-6068, 2003). We did not observe any generalized keratin mutation-specific organization defects as tested by immunofluorescence staining (FIG. 4A). The diseased livers (with or without keratin mutations) had reorganization of the keratins filaments with the most prominent feature being thickening and partial collapse (FIG. 4A, panels d and g) as compared with normal liver keratin staining (FIG. 4A, panel a). The diseased livers had variable but significant vimentin-positive staining (FIG. 4A, panels e, h), which was used as a fibroblast/stellate cell marker, as compared with normal liver (FIG. 4A, panel b). Vimentin staining did not correlate with the presence of keratin mutations, and did not involve hepatocytes (FIG. 4A; merged images c, f, i). Analysis of additional liver samples with proper attention to sample handling will be needed to better assess any potential keratin mutation-induced effects on keratin organization.

We also asked if any histologic features identified by light microscopy could distinguish cirrhotic livers of patients with and without keratin mutations (Ku et al, Proc Natl Acad Sci USA 100:6063-6068, 2003). Features such as Mallory's hyaline, acidophil bodies, enlarged hepatocytes, ground glass cytoplasm and dysplasia were found in keratin-mutant and non-keratin-mutant livers. However, close inspection of the liver specimen(s) showed a unique accumulation in some hepatocytes of cytoplasmic filamentous arrays (FIG. 4B). When coding of the slides (with mutant or nonmutant keratin) was opened, the findings indicated that the filamentous deposits were found in 10 of 17 tested patients with keratin mutations but in only 3 of 16 disease-matched controls (p=0.03). When patients with only primary hepatocellular diseases (cryptogenic, viral hepatitis, alcohol, acute fulminant hepatitis) were included in the analysis, 10 of 11 explants with a keratin mutation contained the cytoplasmic filamentous deposits as compared with 3 of 13 disease-matched controls (p=0.001). The nature of the filamentous deposits remains to be determined, but they do not appear to correspond to aggregated keratins since they were not recognized by anti-keratin antibodies (which may reflect epitope masking, not shown).

Discussion

Mutations in keratins and other IF family members, including lamins, desmin, glial fibrillary acidic protein (GFAP) and neurofilaments, are well-established causes of a wide range of tissue specific human diseases. The list of newly identified diseases associated with IF proteins continues to grow, including the latest association of K8 with liver disease, GFAP with Alexander disease and the neurofilament-L chain with Charcot-Marie-Tooth type-2. One distinguishing feature of K8/K18 mutations, as compared with epidermal keratin mutations involving K5/K14/K1/K10, is that the epidermal keratin diseases are typically autosomal dominant with ~100% penetrance. In contrast, K8/K18 mutations appear to be risk factors with variable penetrance, rather than direct causes of disease. In support of this, the location of the characterized K8/K18 mutations does not involve conserved pan-keratin domain mutation hot spots that have been identified in epidermal keratins (FIG. 5). Apparent absence of such mutations suggests that they may be lethal, given that K8/K18 are among the earliest expressed keratins during embryogenesis. Also, K8/K18 mutations are germline and do not simply result as a consequence of the liver disease (Table 5).

The ages of the offspring with the keratin mutations range from 31-52, but none of these carriers have apparent liver disease, based on clinical history and serologic testing. These observations support a "multi-hit" hypothesis, whereby one major "hit" is carrying a relevant K8/K18 mutation with subsequent "hits" including underlying liver disease or exposure to injurious factors such as toxins or viruses (FIG. 6). Clinical and natural history studies can be used to define the relative risk of subsequent development of liver disease, or the relative increase in progression of an underlying liver disease, in those who carry specific K8/K18 mutations.

At the molecular level mutations in IF chains can, in principle, alter the α-helical propensity of the chains, the number and type of the intra- and inter-helical ionic interactions, increase or decrease the stability of the α-helical strands, modify the helix capping potential and change the hydrogen bonding ability of the chains. Mutations could also adversely affect the ability of the molecules to assemble in to viable IF, to bundle as normally required, or to function properly even if assembled correctly (Table 6). Therefore, potential effects of the keratin mutations include destabilizing K8/K18 filaments, interrupting ionic interactions, introducing disulfide bonds, or altering keratin phosphorylation/solubility. These molecular consequences of keratin mutations may interfere the normal filament reorganizations that occur in hepatocytes upon multiple physiologic and nonphysiologic stimuli, and ultimately result in liver disease (FIG. 6).

TABLE 6

Molecular Consequences of Keratin mutations

| | Mutations | Potential effects |
|---|---|---|
| K8 | R340H | Destabilization |
| | G433S | Altering keratin phosphorylation |
| | R453C | Formation of a disulfide bond |
| | 1-465(I) RDT(468) | Destabilization |
| K18 | Δ 64-71(TGIAGGLA) | Destabilization |
| | E275G | Destabilization |
| | Q284R | Destabilization |
| | T294M | Interruption of ionic interaction |
| | T296I | Interruption of ionic interaction |

The significant number of patients described in this study, with new and previously described K8/K18 mutations, provide several insights into keratin-associated liver diseases. For example, K8 Y53H, K8 G61C, and most prominently K8 R340H are emerging as mutation hot spots. These mutations were found in 5, 6 and 30 of the 58 patients with K8/K18 mutations, respectively (Table 3 and FIG. 5), and collectively make up ~71% of the K8/K18 mutations identified to date, while the K8 R340H mutation alone makes up ~52% of all K8/K18 mutations identified to date. Analysis of additional liver disease patients will help determine if these mutation hot spots maintain their frequency. Also, search for additional keratin mutation carriers in a broad range of cryptogenic and noncryptogenic liver diseases is clearly warranted.

When we initially identified K8 and K18 mutations in 6 patients, all 6 had cryptogenic liver disease (Ku et al, J Clin Invest 99:19-23, 1997 and Ku et al, N Engl J Med 344:1580-1587, 2001). This liver disease makes up nearly 10% of all patients who undergo liver transplantation. In this cryptogenic liver disease cohort 7 of 68 patients (10.3%) have K8 or K18 mutations. However and more importantly, our more significant findings are that keratin mutations are also common (12.8%) in the noncryptogeic liver disease group (Table 2) that accounts for the remaining 90% of liver transplantations (based on the patient groups we studied). The association of keratin mutations with cryptogenic liver disease raises the possibility that some diseases that are linked with this type of cirrhosis, such as nonalcoholic steatohepatitis, may also be associated with keratin mutations. More K8 and/or K18 mutations may be identified as we are in the process of completing the characterization of the entire coding and promoter regions (nearly 95% of K8 and K18 coding regions have been completed).

Although the mechanisms by which keratin mutations predispose to cirrhosis remain to be defined, already known and emerging keratin functions are likely to be involved. For example, multiple transgenic mouse model studies showed that K8/K18 serve the essential function of protecting hepatocytes from a variety of stresses including agents that cause acute (e.g. acetaminophen) or chronic (e.g. griseofulvin) injury, and agents that induce apoptosis (e.g. Fas antibody). K8/K18 may also be involved in protein targeting to the apical compartment of polarized epithelia, interacting with apoptotic machinery proteins, cell signaling and regulating the availability of abundant cellular proteins. Hence, keratin mutations may potentially act at a number of functional cellular nodes. One surrogate marker of keratin function is cytoplasmic filament organization, which was shown to be abnormally altered, only after stress exposure, in the K8 Y53H/G61C mutations (Ku et al, N Engl J Med 344:1580-1587, 2001). Our observation of preferential cytoplasmic filamentous deposits in cirrhotic livers of patients with keratin mutations is likely to be relevant and is reminiscent of Rosenthal fibers that are seen in association with Alexander Disease. The nature and pathogenesis of these deposits and their association with keratin-related liver disease remain to be investigated, but they are morphologically distinct from Mallory body-type deposits.

It is evident that subject invention provides a convenient and effective way of determining whether a patient will be susceptible to liver disease. The subject methods will provide a number of benefits, including preventive treatment and diet. As such, the subject invention represents a significant contribution to the art.

What is claimed is:

1. A method for detecting a predisposition to liver disease in a human, the method comprising:

obtaining a biological sample from a human, and analyzing the biological sample for the presence or absence of one or more mutations in a keratin K8 protein tail domain selected from the group consisting of G433S, R453C, and a combination of any of the foregoing, and detecting a predisposition to liver disease based on the presence of the one or more mutations.

2. The method of claim 1, wherein analyzing the biological sample comprises detecting the presence or absence of K8 G433S.

3. The method of claim 1, wherein analyzing the biological sample comprises the steps of:

amplifying a region of a polynucleotide comprising a nucleotide sequence encoding K8 to provide an amplified fragment; and detecting the presence or absence of a nucleotide sequence encoding the one or more mutations in said amplified fragment.

4. The method of claim 3, wherein detecting the presence or absence of a nucleotide sequence encoding the one or more mutations in said amplified fragment comprises detecting hybridization of a probe specific for a nucleic acid sequence encoding the one or more mutations.

5. The method of claim 1, wherein analyzing the biological sample for the presence or absence of one or more mutations in a keratin K8 protein tail domain comprises contacting a cell, tissue or serum sample from the human with an antibody specific for a K8 protein comprising the one or more mutations.

* * * * *

SEQUENCE LISTING

```
<160> NUMBER OF SEQ ID NOS: 9

<210> SEQ ID NO 1
<211> LENGTH: 1485
<212> TYPE: DNA
<213> ORGANISM: H. sapiens
<220> FEATURE:
<221> NAME/KEY: CDS
<222> LOCATION: (119)...(1408)

<400> SEQUENCE: 1
tccggggcgg gggcggggcc tcactctgcg atataactcg ggtcgcgcgg ctcgcgcagg      60
ccgccaccgt cgtccgcaaa gcctgagtcc tgtcctttct ctctccccgg acagcatg     118 agc ttc acc act cgc tcc acc ttc tcc acc aac tac cgg tcc ctg ggc      166
Ser Phe Thr Thr Arg Ser Thr Phe Ser Thr Asn Tyr Arg Ser Leu Gly
  1               5                   10                  15 tct gtc cag gcg ccc agc tac ggc gcc cgg ccg gtc agc agc gcg gcc      214
Ser Val Gln Ala Pro Ser Tyr Gly Ala Arg Pro Val Ser Ser Ala Ala
             20                  25                  30 agc gtc tat gca ggc gct ggg ggc tct ggt tcc cgg atc tcc gtg tcc      262
Ser Val Tyr Ala Gly Ala Gly Gly Ser Gly Ser Arg Ile Ser Val Ser
         35                  40                  45
```

```
cgc tcc acc agc ttc agg ggc ggc atg ggg tcc ggg ggc ctg gcc acc      310
Arg Ser Thr Ser Phe Arg Gly Gly Met Gly Ser Gly Gly Leu Ala Thr
     50                  55                  60 ggg ata gcc ggg ggt ctg gca gga atg gga ggc atc cag aac gag aag      358
Gly Ile Ala Gly Gly Leu Ala Gly Met Gly Gly Ile Gln Asn Glu Lys
 65                  70                  75                  80 gag acc atg caa agc ctg aac gac cgc ctg gcc tct tac ctg gac aga      406
Glu Thr Met Gln Ser Leu Asn Asp Arg Leu Ala Ser Tyr Leu Asp Arg
                     85                  90                  95 gtg agg agc ctg gag acc gag aac cgg agg ctg gag agc aaa atc cgg      454
Val Arg Ser Leu Glu Thr Glu Asn Arg Arg Leu Glu Ser Lys Ile Arg
                100                 105                 110 gag cac ttg gag aag aag gga ccc cag gtc aga gac tgg agc cat tac      502
Glu His Leu Glu Lys Lys Gly Pro Gln Val Arg Asp Trp Ser His Tyr
            115                 120                 125 ttc aag atc atc gag gac ctg agg gct cag atc ttc gca aat act gtg      550
Phe Lys Ile Ile Glu Asp Leu Arg Ala Gln Ile Phe Ala Asn Thr Val
        130                 135                 140 gac aat gcc cgc atc gtt ctg cag att gac aat gcc cgt ctt gct gct      598
Asp Asn Ala Arg Ile Val Leu Gln Ile Asp Asn Ala Arg Leu Ala Ala
145                 150                 155                 160 gat gac ttt aga gtc aag tat gag aca gag ctg gcc atg cgc cag tct      646
Asp Asp Phe Arg Val Lys Tyr Glu Thr Glu Leu Ala Met Arg Gln Ser
                165                 170                 175 gtg gag aac gac atc cat ggg ctc cgc aag gtc att gat gac acc aat      694
Val Glu Asn Asp Ile His Gly Leu Arg Lys Val Ile Asp Asp Thr Asn
            180                 185                 190 atc aca cga ctg cag ctg gag aca gag atc gag gct ctc aag gag gag      742
Ile Thr Arg Leu Gln Leu Glu Thr Glu Ile Glu Ala Leu Lys Glu Glu
        195                 200                 205 ctg ctc ttc atg aag aag aac cac gaa gag gaa gta aaa ggc cta caa      790
Leu Leu Phe Met Lys Lys Asn His Glu Glu Glu Val Lys Gly Leu Gln
    210                 215                 220 gcc cag att gcc agc tct ggg ttg acc gtg gag gta gat gcc ccc aaa      838
Ala Gln Ile Ala Ser Ser Gly Leu Thr Val Glu Val Asp Ala Pro Lys
225                 230                 235                 240 tct cag gac ctc gcc aag atc atg gca gac atc cgg gcc caa tat gac      886
Ser Gln Asp Leu Ala Lys Ile Met Ala Asp Ile Arg Ala Gln Tyr Asp
                245                 250                 255 gag ctg gct cgg aag aac cga gag gag cta gac aag tac tgg tct cag      934
Glu Leu Ala Arg Lys Asn Arg Glu Glu Leu Asp Lys Tyr Trp Ser Gln
            260                 265                 270 cag att gag gag agc acc aca gtg gtc acc aca cag tct gct gag gtt      982
Gln Ile Glu Glu Ser Thr Thr Val Val Thr Thr Gln Ser Ala Glu Val
        275                 280                 285 gga gct gct gag acg acg ctc aca gag ctg aga cgt aca gtc cag tcc     1030
Gly Ala Ala Glu Thr Thr Leu Thr Glu Leu Arg Arg Thr Val Gln Ser
    290                 295                 300 ttg gag atc gac ctg gac tcc atg aga aat ctg aag gcc agc ttg gag     1078
Leu Glu Ile Asp Leu Asp Ser Met Arg Asn Leu Lys Ala Ser Leu Glu
305                 310                 315                 320 aac agc ctg agg gag gtg gag gcc cgc tac gcc cta cag atg gag cag     1126
Asn Ser Leu Arg Glu Val Glu Ala Arg Tyr Ala Leu Gln Met Glu Gln
                325                 330                 335 ctc aac ggg atc ctg ctg cac ctt gag tca gag ctg gca cag acc cgg     1174
Leu Asn Gly Ile Leu Leu His Leu Glu Ser Glu Leu Ala Gln Thr Arg
            340                 345                 350 gca gag gga cag cgc cag gcc cag gag tat gag gcc ctg ctg aac atc     1222
Ala Glu Gly Gln Arg Gln Ala Gln Glu Tyr Glu Ala Leu Leu Asn Ile
        355                 360                 365
```

-continued

```
aag gtc aag ctg gag gct gag atc gcc acc tac cgc cgc ctg ctg gaa      1270
Lys Val Lys Leu Glu Ala Glu Ile Ala Thr Tyr Arg Arg Leu Leu Glu
    370             375                 380 gat ggc gag gac ttt aat ctt ggt gat gcc ttg gac agc agc aac tcc      1318
Asp Gly Glu Asp Phe Asn Leu Gly Asp Ala Leu Asp Ser Ser Asn Ser
385             390                 395                 400 atg caa acc atc caa aag acc acc acc cgc cgg ata gtg gat ggc aaa      1366
Met Gln Thr Ile Gln Lys Thr Thr Thr Arg Arg Ile Val Asp Gly Lys
                405                 410                 415 gtg gtg tct gag acc aat gac acc aaa gtt ctg agg cat taa              1408
Val Val Ser Glu Thr Asn Asp Thr Lys Val Leu Arg His *
            420                 425 gccagcagaa gcagggtacc ctttggggag caggaggcca ataaaagtt cagagttcaa     1468 aaaaaaaaaa aaaaaaa                                                    1485

<210> SEQ ID NO 2
<211> LENGTH: 429
<212> TYPE: PRT
<213> ORGANISM: H. sapiens

<400> SEQUENCE: 2

Ser Phe Thr Thr Arg Ser Thr Phe Ser Thr Asn Tyr Arg Ser Leu Gly
1               5                   10                  15

Ser Val Gln Ala Pro Ser Tyr Gly Ala Arg Pro Val Ser Ala Ala
            20                  25                  30

Ser Val Tyr Ala Gly Ala Gly Gly Ser Gly Ser Arg Ile Ser Val Ser
            35                  40                  45

Arg Ser Thr Ser Phe Arg Gly Gly Met Gly Ser Gly Gly Leu Ala Thr
    50                  55                  60

Gly Ile Ala Gly Gly Leu Ala Gly Met Gly Gly Ile Gln Asn Glu Lys
65              70                  75                  80

Glu Thr Met Gln Ser Leu Asn Asp Arg Leu Ala Ser Tyr Leu Asp Arg
                85                  90                  95

Val Arg Ser Leu Glu Thr Glu Asn Arg Arg Leu Glu Ser Lys Ile Arg
            100                 105                 110

Glu His Leu Glu Lys Lys Gly Pro Gln Val Arg Asp Trp Ser His Tyr
        115                 120                 125

Phe Lys Ile Ile Glu Asp Leu Arg Ala Gln Ile Phe Ala Asn Thr Val
    130                 135                 140

Asp Asn Ala Arg Ile Val Leu Gln Ile Asp Asn Ala Arg Leu Ala Ala
145                 150                 155                 160

Asp Asp Phe Arg Val Lys Tyr Glu Thr Glu Leu Ala Met Arg Gln Ser
                165                 170                 175

Val Glu Asn Asp Ile His Gly Leu Arg Lys Val Ile Asp Asp Thr Asn
            180                 185                 190

Ile Thr Arg Leu Gln Leu Glu Thr Glu Ile Glu Ala Leu Lys Glu Glu
        195                 200                 205

Leu Leu Phe Met Lys Lys Asn His Glu Glu Glu Val Lys Gly Leu Gln
    210                 215                 220

Ala Gln Ile Ala Ser Ser Gly Leu Thr Val Glu Val Asp Ala Pro Lys
225                 230                 235                 240

Ser Gln Asp Leu Ala Lys Ile Met Ala Asp Ile Arg Ala Gln Tyr Asp
                245                 250                 255

Glu Leu Ala Arg Lys Asn Arg Glu Glu Leu Asp Lys Tyr Trp Ser Gln
            260                 265                 270
```

```
Gln Ile Glu Glu Ser Thr Thr Val Thr Thr Gln Ser Ala Glu Val
        275                 280                 285

Gly Ala Ala Glu Thr Thr Leu Thr Glu Leu Arg Arg Thr Val Gln Ser
290                 295                 300

Leu Glu Ile Asp Leu Asp Ser Met Arg Asn Leu Lys Ala Ser Leu Glu
305                 310                 315                 320

Asn Ser Leu Arg Glu Val Glu Ala Arg Tyr Ala Leu Gln Met Glu Gln
                325                 330                 335

Leu Asn Gly Ile Leu Leu His Leu Glu Ser Glu Leu Ala Gln Thr Arg
            340                 345                 350

Ala Glu Gly Gln Arg Gln Ala Gln Glu Tyr Glu Ala Leu Leu Asn Ile
        355                 360                 365

Lys Val Lys Leu Glu Ala Glu Ile Ala Thr Tyr Arg Arg Leu Leu Glu
370                 375                 380

Asp Gly Glu Asp Phe Asn Leu Gly Asp Ala Leu Asp Ser Ser Asn Ser
385                 390                 395                 400

Met Gln Thr Ile Gln Lys Thr Thr Thr Arg Arg Ile Val Asp Gly Lys
                405                 410                 415

Val Val Ser Glu Thr Asn Asp Thr Lys Val Leu Arg His
            420                 425

<210> SEQ ID NO 3
<211> LENGTH: 1752
<212> TYPE: DNA
<213> ORGANISM: H. sapiens
<220> FEATURE:
<221> NAME/KEY: CDS
<222> LOCATION: (63)...(1511)

<400> SEQUENCE: 3
ctgctccttc taggatctcc gcctggttcg gcccgcctgc ctccactcct gcctccacca    60 tg tcc atc agg gtg acc cag aag tcc tac aag gtg tcc acc tct ggc     107
   Ser Ile Arg Val Thr Gln Lys Ser Tyr Lys Val Ser Thr Ser Gly
   1               5                   10                  15 ccc cgg gcc ttc agc agc cgc tcc tac acg agt ggg ccc ggt tcc cgc     155
Pro Arg Ala Phe Ser Ser Arg Ser Tyr Thr Ser Gly Pro Gly Ser Arg
                20                  25                  30 atc agc tcc tcg agc ttc tcc cga gtg ggc agc agc aac ttt cgc ggt     203
Ile Ser Ser Ser Ser Phe Ser Arg Val Gly Ser Ser Asn Phe Arg Gly
            35                  40                  45 ggc ctg ggc ggc ggc tat ggt ggg gcc agc ggt atg gga ggc atc acc     251
Gly Leu Gly Gly Gly Tyr Gly Gly Ala Ser Gly Met Gly Gly Ile Thr
        50                  55                  60 gca gtt acg gtc aac cag agc ctg ctg agc ccc ctt gtc ctg gag gtg     299
Ala Val Thr Val Asn Gln Ser Leu Leu Ser Pro Leu Val Leu Glu Val
65                  70                  75 gac ccc aac atc cag gcc gtg cgc acc cag gag aag gag cag atc aag     347
Asp Pro Asn Ile Gln Ala Val Arg Thr Gln Glu Lys Glu Gln Ile Lys
 80                  85                  90                  95 acc ctc aac aac aag ttt gcc tcc ttc ata gac aag gta cgg ttc ctg     395
Thr Leu Asn Asn Lys Phe Ala Ser Phe Ile Asp Lys Val Arg Phe Leu
                100                 105                 110 gag cag cag aac aag atg ctg gag acc aag tgg agc ctc ctg cag cag     443
Glu Gln Gln Asn Lys Met Leu Glu Thr Lys Trp Ser Leu Leu Gln Gln
            115                 120                 125 cag aag acg gct cga agc aac atg gac aac atg ttc gag agc tac atc     491
Gln Lys Thr Ala Arg Ser Asn Met Asp Asn Met Phe Glu Ser Tyr Ile
        130                 135                 140 aac aac ctt agg cgg cag ctg gag act ctg ggc cag gag aag ctg aag     539
```

```
                Asn Asn Leu Arg Arg Gln Leu Glu Thr Leu Gly Gln Glu Lys Leu Lys
                145                 150                 155 ctg gag gcg gag ctt ggc aac atg cag ggg ctg gtg gag gac ttc aag          587
Leu Glu Ala Glu Leu Gly Asn Met Gln Gly Leu Val Glu Asp Phe Lys
160                 165                 170                 175 aac aag tat gag gat gag atc aat aag cgt aca gag atg gag aac gaa          635
Asn Lys Tyr Glu Asp Glu Ile Asn Lys Arg Thr Glu Met Glu Asn Glu
                180                 185                 190 ttt gtc ctc atc aag aag gat gtg gat gaa gct tac atg aac aag gta          683
Phe Val Leu Ile Lys Lys Asp Val Asp Glu Ala Tyr Met Asn Lys Val
                195                 200                 205 gag ctg gag tct cgc ctg gaa ggg ctg acc gac gag atc aac ttc ctc          731
Glu Leu Glu Ser Arg Leu Glu Gly Leu Thr Asp Glu Ile Asn Phe Leu
210                 215                 220 agg cag cta tat gaa gag gag atc cgg gag ctg cag tcc cag atc tcg          779
Arg Gln Leu Tyr Glu Glu Glu Ile Arg Glu Leu Gln Ser Gln Ile Ser
        225                 230                 235 gac aca tct gtg gtg ctg tcc atg gac aac agc cgc tcc ctg gac atg          827
Asp Thr Ser Val Val Leu Ser Met Asp Asn Ser Arg Ser Leu Asp Met
240                 245                 250                 255 gac agc atc att gct gag gtc aag gca cag tac gag gat att gcc aac          875
Asp Ser Ile Ile Ala Glu Val Lys Ala Gln Tyr Glu Asp Ile Ala Asn
                260                 265                 270 cgc agc cgg gct gag gct gag agc atg tac cag atc aag tat gag gag          923
Arg Ser Arg Ala Glu Ala Glu Ser Met Tyr Gln Ile Lys Tyr Glu Glu
                275                 280                 285 ctg cag agc ctg gct ggg aag cac ggg gat gac ctg cgg cgc aca aag          971
Leu Gln Ser Leu Ala Gly Lys His Gly Asp Asp Leu Arg Arg Thr Lys
        290                 295                 300 act gag atc tct gag atg aac cgg aac atc agc cgg ctc cag gct gag         1019
Thr Glu Ile Ser Glu Met Asn Arg Asn Ile Ser Arg Leu Gln Ala Glu
305                 310                 315 att gag ggc ctc aaa ggc cag agg gct tcc ctg gag gcc gcc att gca         1067
Ile Glu Gly Leu Lys Gly Gln Arg Ala Ser Leu Glu Ala Ala Ile Ala
320                 325                 330                 335 gat gcc gag cag cgt gga gag ctg gcc att aag gat gcc aac gcc aag         1115
Asp Ala Glu Gln Arg Gly Glu Leu Ala Ile Lys Asp Ala Asn Ala Lys
                340                 345                 350 ttg tcc gag ctg gag gcc gcc ctg cag cgg gcc aag cag gac atg gcg         1163
Leu Ser Glu Leu Glu Ala Ala Leu Gln Arg Ala Lys Gln Asp Met Ala
                355                 360                 365 cgg cag ctg cgt gag tac cag gag ctg atg aac gtc aag ctg gcc ctg         1211
Arg Gln Leu Arg Glu Tyr Gln Glu Leu Met Asn Val Lys Leu Ala Leu
        370                 375                 380 gac atc gag atc gcc acc tac agg aag ctg ctg gag ggc gag gag agc         1259
Asp Ile Glu Ile Ala Thr Tyr Arg Lys Leu Leu Glu Gly Glu Glu Ser
385                 390                 395 cgg ctg gag tct ggg atg cag aac atg agt att cat acg aag acc acc         1307
Arg Leu Glu Ser Gly Met Gln Asn Met Ser Ile His Thr Lys Thr Thr
400                 405                 410                 415 agc ggc tat gca ggt ggt ctg agc tcg gcc tat ggg ggc ctc aca agc         1355
Ser Gly Tyr Ala Gly Gly Leu Ser Ser Ala Tyr Gly Gly Leu Thr Ser
                420                 425                 430 ccc ggc ctc agc tac agc ctg ggc tcc agc ttt ggc tct ggc gcg ggc         1403
Pro Gly Leu Ser Tyr Ser Leu Gly Ser Ser Phe Gly Ser Gly Ala Gly
                435                 440                 445 tcc agc tcc ttc agc cgc acc agc tcc tcc agg gcc gtg gtt gtg aag         1451
Ser Ser Ser Phe Ser Arg Thr Ser Ser Ser Arg Ala Val Val Val Lys
        450                 455                 460 aag atc gag aca cgt gat ggg aag ctg gtg tct gag tcc tct gac gtc         1499
```

```
Lys Ile Glu Thr Arg Asp Gly Lys Leu Val Ser Glu Ser Ser Asp Val
465                 470                 475 ctg ccc aag tga acagctgcgg cagccctcc cagcctaccc ctcctgcgct          1551
Leu Pro Lys *
480 gccccagagc ctgggaagga ggccgctatg cagggtagca ctgggaacag gagacccacc   1611 tgaggctcag ccctagccct cagcccacct ggggagttta ctacctgggg accccccttg   1671 cccatgcctc cagctacaaa acaattcaat tgcttttttt ttttggtcca aaataaaacc   1731 tcagctagct ctgccaaacc c                                             1752

<210> SEQ ID NO 4
<211> LENGTH: 482
<212> TYPE: PRT
<213> ORGANISM: H. sapiens

<400> SEQUENCE: 4

Ser Ile Arg Val Thr Gln Lys Ser Tyr Lys Val Ser Thr Ser Gly Pro
1               5                   10                  15

Arg Ala Phe Ser Ser Arg Ser Tyr Thr Ser Gly Pro Gly Ser Arg Ile
            20                  25                  30

Ser Ser Ser Ser Phe Ser Arg Val Gly Ser Ser Asn Phe Arg Gly Gly
        35                  40                  45

Leu Gly Gly Gly Tyr Gly Gly Ala Ser Gly Met Gly Gly Ile Thr Ala
    50                  55                  60

Val Thr Val Asn Gln Ser Leu Leu Ser Pro Leu Val Leu Glu Val Asp
65                  70                  75                  80

Pro Asn Ile Gln Ala Val Arg Thr Gln Glu Lys Glu Gln Ile Lys Thr
                85                  90                  95

Leu Asn Asn Lys Phe Ala Ser Phe Ile Asp Lys Val Arg Phe Leu Glu
            100                 105                 110

Gln Gln Asn Lys Met Leu Glu Thr Lys Trp Ser Leu Leu Gln Gln Gln
        115                 120                 125

Lys Thr Ala Arg Ser Asn Met Asp Asn Met Phe Glu Ser Tyr Ile Asn
    130                 135                 140

Asn Leu Arg Arg Gln Leu Glu Thr Leu Gly Gln Glu Lys Leu Lys Leu
145                 150                 155                 160

Glu Ala Glu Leu Gly Asn Met Gln Gly Leu Val Glu Asp Phe Lys Asn
                165                 170                 175

Lys Tyr Glu Asp Glu Ile Asn Lys Arg Thr Glu Met Glu Asn Glu Phe
            180                 185                 190

Val Leu Ile Lys Lys Asp Val Asp Glu Ala Tyr Met Asn Lys Val Glu
        195                 200                 205

Leu Glu Ser Arg Leu Glu Gly Leu Thr Asp Glu Ile Asn Phe Leu Arg
    210                 215                 220

Gln Leu Tyr Glu Glu Glu Ile Arg Glu Leu Gln Ser Gln Ile Ser Asp
225                 230                 235                 240

Thr Ser Val Val Leu Ser Met Asp Asn Ser Arg Ser Leu Asp Met Asp
                245                 250                 255

Ser Ile Ile Ala Glu Val Lys Ala Gln Tyr Glu Asp Ile Ala Asn Arg
            260                 265                 270

Ser Arg Ala Glu Ala Glu Ser Met Tyr Gln Ile Lys Tyr Glu Glu Leu
        275                 280                 285

Gln Ser Leu Ala Gly Lys His Gly Asp Asp Leu Arg Arg Thr Lys Thr
    290                 295                 300
```

-continued

```
Glu Ile Ser Glu Met Asn Arg Asn Ile Ser Arg Leu Gln Ala Glu Ile
305                 310                 315                 320
Glu Gly Leu Lys Gly Gln Arg Ala Ser Leu Glu Ala Ala Ile Ala Asp
            325                 330                 335
Ala Glu Gln Arg Gly Glu Leu Ala Ile Lys Asp Ala Asn Ala Lys Leu
        340                 345                 350
Ser Glu Leu Glu Ala Ala Leu Gln Arg Ala Lys Gln Asp Met Ala Arg
    355                 360                 365
Gln Leu Arg Glu Tyr Gln Glu Leu Met Asn Val Lys Leu Ala Leu Asp
370                 375                 380
Ile Glu Ile Ala Thr Tyr Arg Lys Leu Leu Glu Gly Glu Glu Ser Arg
385                 390                 395                 400
Leu Glu Ser Gly Met Gln Asn Met Ser Ile His Thr Lys Thr Thr Ser
            405                 410                 415
Gly Tyr Ala Gly Gly Leu Ser Ser Ala Tyr Gly Gly Leu Thr Ser Pro
        420                 425                 430
Gly Leu Ser Tyr Ser Leu Gly Ser Ser Phe Gly Ser Gly Ala Gly Ser
    435                 440                 445
Ser Ser Phe Ser Arg Thr Ser Ser Arg Ala Val Val Val Lys Lys
    450                 455                 460
Ile Glu Thr Arg Asp Gly Lys Leu Val Ser Glu Ser Ser Asp Val Leu
465                 470                 475                 480
Pro Lys

<210> SEQ ID NO 5
<211> LENGTH: 26
<212> TYPE: DNA
<213> ORGANISM: H. sapiens

<400> SEQUENCE: 5
atgccgagca gcgtggagag ctggcc                                         26

<210> SEQ ID NO 6
<211> LENGTH: 7
<212> TYPE: PRT
<213> ORGANISM: H. sapiens

<400> SEQUENCE: 6

Ala Glu Gln Arg Gly Glu Leu
 1               5

<210> SEQ ID NO 7
<211> LENGTH: 26
<212> TYPE: DNA
<213> ORGANISM: H. sapiens
<220> FEATURE:
<221> NAME/KEY: mutation
<222> LOCATION: 13
<223> OTHER INFORMATION: N = any nucleotide

<400> SEQUENCE: 7
atgccgagca gcntggagag ctggcc                                         26

<210> SEQ ID NO 8
<211> LENGTH: 7
<212> TYPE: PRT
<213> ORGANISM: H. sapiens
<220> FEATURE:
<221> NAME/KEY: VARIANT
<222> LOCATION: 4
<223> OTHER INFORMATION: Xaa = R or H
```

```
<400> SEQUENCE: 8

Ala Glu Gln Xaa Gly Glu Leu
 1               5

<210> SEQ ID NO 9
<211> LENGTH: 14
<212> TYPE: PRT
<213> ORGANISM: H. sapiens

<400> SEQUENCE: 9

Ile Ala Asp Ala Glu Gln Arg Gly Glu Leu Ala Ile Lys Asp
 1               5                  10
```